(12) United States Patent
Dinca et al.

(10) Patent No.: US 11,953,482 B2
(45) Date of Patent: Apr. 9, 2024

(54) COMPOSITIONS AND METHODS FOR CARBON DIOXIDE SENSING

(71) Applicant: Massachusetts Institute of Technology, Cambridge, MA (US)

(72) Inventors: Mircea Dinca, Belmont, MA (US); Ivo Stassen, Boston, MA (US); Jinhu Dou, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 954 days.

(21) Appl. No.: 16/850,534

(22) Filed: Apr. 16, 2020

(65) Prior Publication Data

US 2020/0333306 A1  Oct. 22, 2020

Related U.S. Application Data

(60) Provisional application No. 62/836,001, filed on Apr. 18, 2019.

(51) Int. Cl.
| | | |
|---|---|---|
| G01N 33/00 | (2006.01) | |
| B01J 20/22 | (2006.01) | |
| B01J 20/28 | (2006.01) | |
| C07F 1/00 | (2006.01) | |
| G01N 27/04 | (2006.01) | |
| G01N 27/12 | (2006.01) | |

(52) U.S. Cl.
CPC ............ *G01N 33/004* (2013.01); *B01J 20/22* (2013.01); *B01J 20/226* (2013.01); *B01J 20/28078* (2013.01); *C07F 1/005* (2013.01); *G01N 27/04* (2013.01); *G01N 27/126* (2013.01)

(58) Field of Classification Search
CPC .... G01N 33/004; G01N 27/04; G01N 27/126; B01J 20/22; B01J 20/226; B01J 20/28078; C07F 1/005
See application file for complete search history.

(56) References Cited

U.S. PATENT DOCUMENTS

| | | |
|---|---|---|
| 2012/0297982 A1 | 11/2012 | Dinca et al. |
| 2017/0073364 A1 | 3/2017 | Dinca et al. |
| 2017/0341010 A1 | 11/2017 | Dinca et al. |
| 2018/0011010 A1* | 1/2018 | Chang ................ B01J 20/28097 |
| 2018/0093218 A1 | 4/2018 | Eddaoudi et al. |
| 2018/0304246 A1 | 10/2018 | Eddaoudi et al. |

FOREIGN PATENT DOCUMENTS

| | | | |
|---|---|---|---|
| WO | WO 2013/144628 A1 | 10/2013 | |
| WO | WO-2016174468 A1 * | 11/2016 | ............. B01D 53/02 |

OTHER PUBLICATIONS

Bag et al.(hereinafter Bag) "A PCB based Chemiresistive carbon dioxide sensor operating at room temperature under different relative humidity", IEEE 13th Nanotechnology Materials and Devices Conference (NMDC), 2018. (Year: 2018).*

(Continued)

*Primary Examiner* — Farhana A Hoque
*Assistant Examiner* — Dilara Sultana
(74) *Attorney, Agent, or Firm* — Wolf, Greenfield & Sacks, P.C.

(57) ABSTRACT

Methods of sensing carbon dioxide, sensors, and related articles and systems are generally described.

25 Claims, 6 Drawing Sheets

(56) References Cited

OTHER PUBLICATIONS

W.-Y. Chuang, C.-C. Wu, S.-S. Lu and C.-T. Lin, "A printable conductive polymer CO2 sensor with high selectivity to humidity," 2017 19th International Conference on Solid-State Sensors, Actuators and Microsystems (Transducers), Kaohsiung, Taiwan, 2017, pp. 1501-1503, (Year: 2017).*
Campbell et al., Chemiresistive Sensor Arrays from Conductive 2D Metal-Organic Frameworks. J Am Chem Soc. Nov. 4, 2015;137(43):13780-3. doi: 10.1021/jacs.5b09600. Epub Oct. 27, 2015. PMID: 26456526.
Latif et al., Graphene Hybrid Materials in Gas Sensing Applications. Sensors (Basel). Dec. 4, 2015;15(12):30504-24. doi: 10.3390/s151229814. PMID: 26690156; PMCID: PMC4721734.
Campbell et al., $Cu_3$(hexaiminotriphenylene)$_2$: an electrically conductive 2D metal-organic framework for chemiresistive sensing. Angew Chem Int Ed Engl. Mar. 27, 2015;54(14):4349-52. doi: 10.1002/anie.201411854. Epub Feb. 9, 2015. PMID: 25678397.
Stassen et al., An updated roadmap for the integration of metal-organic frameworks with electronic devices and chemical sensors. Chem Soc Rev. Jun. 6, 2017;46(11):3185-3241. doi: 10.1039/c7cs00122c. PMID: 28452388.
Sun et al., Electrically Conductive Porous Metal-Organic Frameworks. Angew Chem Int Ed Engl. Mar. 7, 2016;55(11):3566-79. doi: 10.1002/anie.201506219. Epub Jan. 8, 2016. PMID: 26749063.
Zhao et al., Two-dimensional metal-organic framework nanosheets: synthesis and applications. Chem Soc Rev. Aug. 13, 2018;47(16):6267-6295. doi: 10.1039/c8cs00268a. PMID: 29971309.

\* cited by examiner

COMPOSITIONS AND METHODS FOR CARBON DIOXIDE SENSING

RELATED APPLICATIONS

This application claims priority under 35 U.S.C. § 119(e) to U.S. Provisional Application No. 62/836,001, filed Apr. 18, 2019, and entitled "Compositions and Methods for Carbon Dioxide Sensing", which is incorporated herein by reference in its entirety for all purposes.

TECHNICAL FIELD

Sensors configured to sense carbon dioxide, methods of sensing carbon dioxide, and associated articles and compositions are generally provided.

BACKGROUND

Many current sensors for carbon dioxide exhibit different responses to the same amount of carbon dioxide in different ambient humidities. This makes accurately determining the amount of carbon dioxide in an ambient gas or liquid challenging.

Accordingly, new sensors and methods for sensing carbon dioxide are needed.

SUMMARY

Methods of sensing carbon dioxide, sensors, and related articles and systems are generally described.

In some embodiments, a method of sensing carbon dioxide is provided. The method comprises exposing a composition to a gas or liquid. The composition comprises a molecular structure comprising an electrically conductive backbone, a plurality of heteroatoms, and a plurality of pores. The composition has a monolayer amount of water of greater than or equal to 2 wt %. The gas or liquid comprises carbon dioxide. The gas has a relative humidity of greater than 0% RH or the liquid has a relative humidity of greater than 0% ERH.

In some embodiments, a method of sensing carbon dioxide is provided. The method comprises exposing a metal-organic framework to a gas or liquid. The metal-organic framework comprises a plurality of metal ions, each coordinated with at least one ligand comprising at least two sets of ortho-diimine groups arranged about an organic core. The gas has a relative humidity of greater than 0% RH or the liquid has a relative humidity of greater than 0% ERH. The gas or liquid comprises carbon dioxide.

In some embodiments, a method of sensing carbon dioxide is provided. The method comprises exposing a metal-organic framework to a gas or liquid. The gas has a relative humidity of from 1% RH to 100% RH or the liquid has an equilibrium relative humidity of from 1% ERH to 100% ERH. The gas or liquid comprises carbon dioxide. The metal-organic framework exhibits a change in electrical resistivity that is directly proportional to an amount of carbon dioxide in the gas or liquid.

In some embodiments, a sensor is provided. The sensor comprises a composition. The composition comprises a molecular structure comprising an electrically conductive backbone, a plurality of heteroatoms, and a plurality of pores. The composition has a monolayer amount of water of greater than or equal to 2 wt %. The composition is configured to exhibit a change in electrical resistivity upon exposure to a gas comprising carbon dioxide and having a relative humidity of greater than 0% RH or upon exposure to a liquid comprising carbon dioxide and having an equilibrium relative humidity of greater than 0% ERH.

In some embodiments, a sensor is provided. The sensor comprises a metal-organic framework. The metal-organic framework comprises a plurality of metal ions, each coordinated with at least one ligand comprising at least two sets of ortho-diimine groups arranged about an organic core. The metal-organic framework is configured to exhibit a change in electrical resistivity upon exposure to a gas comprising carbon dioxide and having a relative humidity of greater than 0% RH or upon exposure to a liquid comprising carbon dioxide and having an equilibrium relative humidity of greater than 0% ERH.

In some embodiments, a sensor is provided. The sensor comprises a metal-organic framework. The metal-organic framework is configured to exhibit a change in electrical resistivity upon exposure to a gas comprising carbon dioxide and having a humidity of greater than 0% RH or upon exposure to a liquid comprising carbon dioxide and having an equilibrium relative humidity of greater than 0% ERH. The change in electrical resistivity is directly proportional to an amount of carbon dioxide in the gas when the relative humidity of the gas is from 20% RH to 80% RH or the change in electrical resistivity is directly proportional to an amount of carbon dioxide in the liquid when the equilibrium relative humidity of the liquid is from 20% ERH to 80% ERH.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
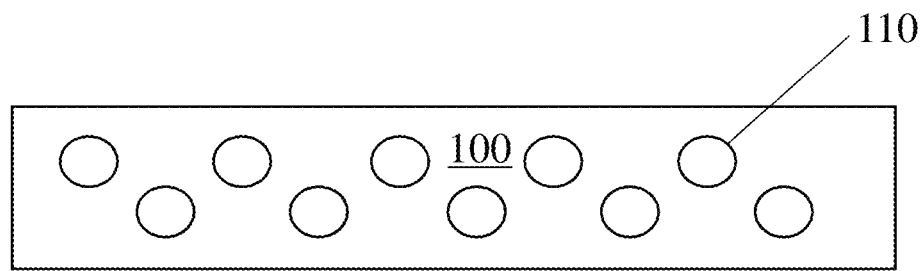
FIG. 1 shows a composition suitable for sensing carbon dioxide, in accordance with some embodiments.

Methods of sensing carbon dioxide, sensors, and associated articles, systems, and methods are generally provided. Some embodiments relate to methods of sensing carbon dioxide that employ compositions, such as metal-organic frameworks, that interact with ambient water (e.g., in the form of ambient humidity) in a manner that promotes advantageous sensing of carbon dioxide. By way of example, in some embodiments, a composition comprises one or more portions that is readily hydrated in the presence of ambient water. Hydration of the composition, and/or one or more portion(s) thereof, may enhance the ability of the composition and/or portion(s) thereof to interact with carbon dioxide, which may enhance the sensitivity of the composition to carbon dioxide. For instance, the presence of water adsorbed onto the composition may promote hydration and/or hydrolysis of carbon dioxide adsorbed onto the composition and/or may promote proton hopping, each of which may enhance the sensitivity of the sensor to the carbon dioxide. As another example, in some embodiments, a composition comprises one or more portions that are hydrated to a relatively constant degree across a range of ambient amounts of water. Such compositions may beneficially interact with carbon dioxide in a relatively consistent manner across this range of ambient amounts of water.

In some embodiments, a composition suitable for sensing carbon dioxide comprises a plurality of pores that are readily hydrated to a relatively constant degree. The plurality of pores may have a hydrophilicity and/or size that promotes the adsorption of water thereonto. For instance, the plurality of pores may readily adsorb water from the ambient environment (e.g., from ambient humidity) and/or may readily become fully hydrated from water in the ambient environment. As another example, the pores may be relatively small (e.g., they may be nanometer scale or sub-nanometer scale). In some embodiments, a composition comprises a plurality of pores that are both hydrophilic and relatively small (e.g., that cause the composition as a whole to uptake a monolayer amount of water that is relatively large and that are nanometer scale or sub-nanometer scale).

In some embodiments, a composition suitable for sensing carbon dioxide comprises a metal-organic framework. Without wishing to be bound by any particular theory, it is believed that metal-organic frameworks may be particularly suited to forming compositions comprising a plurality of pores that are readily hydrated to a relatively constant degree because their components may be selected to be relatively hydrophilic and because they typically form nanometer scale pores and/or sub-nanometer scale pores. For instance, a metal-organic framework may comprise ligands chemically bonded to metal ions to form a porous two- or three-dimensional structure. This porous structure may comprise a plurality of pores with average diameters on the length scale of the distance between the metal ions (and/or on the length scale of the ligands bonded to the metal ions), which is typically nanometer scale or sub-nanometer scale. Hydrophilic metal ions and/or hydrophilic ligands may cause these pores to be hydrophilic and/or be readily hydrated to a relatively constant degree. Moreover, metal-organic frameworks comprising a plurality pores typically have a relatively high density of pores. The pores may form a periodic structure separated only by ligands, and so may be separated from each other by distances on the order of nanometers or Angstroms. As it is believed that a plurality of pores that is relatively hydrophilic, relatively small, and relatively high density may advantageously undergo rapid full hydration in ambient environments having a range of water contents (e.g., having a range of relative humidities and/or equilibrium relative humidities), metal-organic frameworks comprising such pores may be advantageous.

Compositions suitable for use in the sensors described herein may, as a whole, exhibit one or more physical properties that evidence their utility. For instance, in some embodiments, a composition suitable for use in a sensor exhibits a change in electrical resistivity that is directly proportional to an amount of carbon dioxide to which it is exposed. As another example, the change in electrical resistivity upon exposure to carbon dioxide may, additionally or alternatively, be relatively insensitive to the amount of water in the ambient environment (e.g., to the ambient humidity, to the ambient equilibrium relative humidity). These properties may enhance the ease with which measured changes in electrical resistivity of the composition can be correlated to changes in the concentration of carbon dioxide in the ambient environment in which the sensor is positioned.

Some embodiments relate to sensors comprising compositions advantageous for carbon dioxide sensing. Such sensors comprise the relevant composition, and may optionally comprise one or more further components configured to output one or more properties of the composition (e.g., its electrical resistivity) in a form that is readily accessible by other scientific instrumentation and/or by individuals observing the sensor (e.g., visually). By way of example, a sensor may further comprise one or more electrodes, a substrate, one or more components configured to communicate with a computing device, etc. For instance, a sensor may comprise a composition described herein disposed across two or more electrodes and one or more further components configured to measure the electrical resistivity across the electrodes. Other configurations for sensors are also contemplated and described further elsewhere herein.

Some embodiments relate to methods of sensing carbon dioxide. A suitable method may comprise exposing a composition to carbon dioxide. The carbon dioxide may be present in a gas or a liquid that may comprise one or more other, further species. The further species may be species with which carbon dioxide is typically provided (e.g., other gas(es), other liquid(s)), species present in gases or liquids in which it may be desirable to sense carbon dioxide (e.g., species present in air), and/or species that enhance the sensitivity of the composition to carbon dioxide (e.g., as described above, water). By way of example, in some embodiments, a method of sensing carbon dioxide comprises exposing a composition to a gas or liquid comprising carbon dioxide that further comprises water (e.g., a gas with a relative humidity of greater than 0% RH, a liquid with an equilibrium relative humidity of greater than 0% ERH). The gas or liquid may comprise both water and air in some cases.

Some methods may also comprise determining a change in the electrical resistivity of the composition upon exposure to the gas or liquid and/or determining an amount of carbon dioxide in the gas or liquid (e.g., based on the change in electrical resistivity of the composition).

FIG. 1 shows one non-limiting embodiment of a composition suitable for sensing carbon dioxide. In FIG. 1, a composition 100 comprises a plurality of pores 110. The plurality of pores may be uniformly sized and/or spaced, like the pores shown in FIG. 1, or may comprise pores having a variety of sizes and/or spacings. It should also be understood that the other features of the plurality of pores shown in FIG. 1, including the density of pores and the volume fraction of pores in the composition, are merely exemplary, that some embodiments may include pores similar to those shown in FIG. 1 in one or more ways, and that some embodiments may include pores differing from those shown in FIG. 1 in one or more ways.

Figure 2:
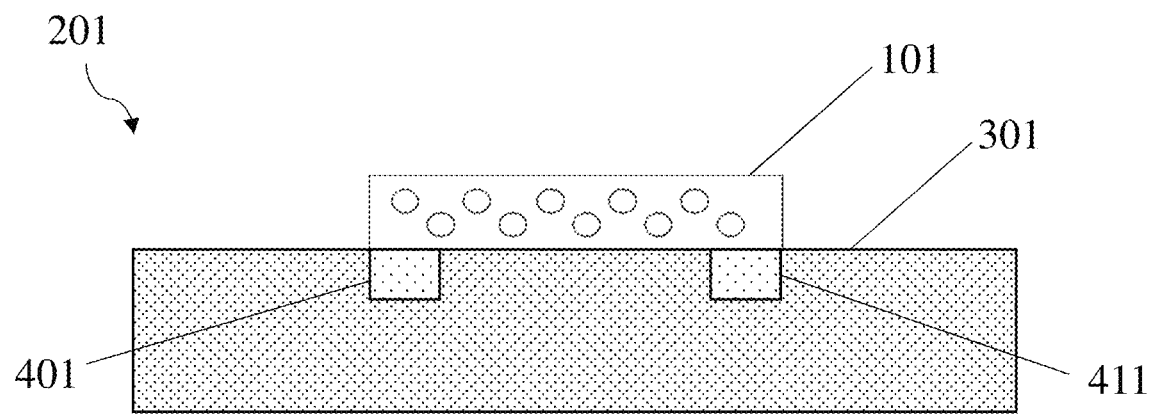
FIG. 2 shows a sensor, in accordance with some embodiments.

As described elsewhere herein, in some embodiments, a composition suitable for sensing carbon dioxide forms a component of a sensor. FIG. 2 shows one non-limiting embodiment of a sensor 201 comprising a composition 101. The sensor shown in FIG. 2 further comprises a substrate 301 and electrodes 401 and 411. The substrate may support the composition and/or other components of the sensor (e.g., one or more electrodes).

In some embodiments, a sensor comprises a substrate is electrically insulating. Other suitable types of substrates include silicon dies, ceramic dies, glass dies, circuit boards, paper sheets, polymer sheets, and polymer foils. Some substrates may comprise one or more coatings (e.g., one or more insulating coatings, one or more conductive coatings, one or more coatings in the form of a film). In some embodiments, two or more substrates are stacked on top of each other to form a composite substrate. The substrate and/or composite substrate may be flexible or rigid.

As for FIG. 1, it should be understood that FIG. 2 is also exemplary and that some sensors may be similar to the sensor shown in FIG. 2 in one or more ways and that some sensors may differ from the sensor shown in FIG. 2 in one or more ways. By way of example, some sensors may comprise each of the components shown in FIG. 2, some sensors may comprise a subset of these components, and some sensors may comprise further components not shown in FIG. 2. As an additional example, some sensors may comprise the components shown in FIG. 2 arranged in a different manner (e.g., the composition and/or electrodes may have a different shape than the composition and electrodes shown in FIG. 2, the electrodes may have different positioning than shown in FIG. 2, etc.).

Non-limiting examples of suitable sensor designs include two-terminal sensors (e.g., resistor/capacitor, source-drain), three terminal sensors (e.g., field-effect transistor, source-drain-gate), and combinations thereof. In some embodiments, a sensor may comprise a Wheatstone bridge, a Kelvin bridge, and/or a suspended-gate field-effect transistor.

The sensors described herein may be fabricated by a variety of suitable methods, non-limiting examples of which include screen printing, lithographic printing, shadow-mask deposition, and ink jet printing. The sensors may comprise thin films and/or thick films (e.g., thin films and/or thick films formed by one or more of the previously-mentioned techniques).

Figure 3A:
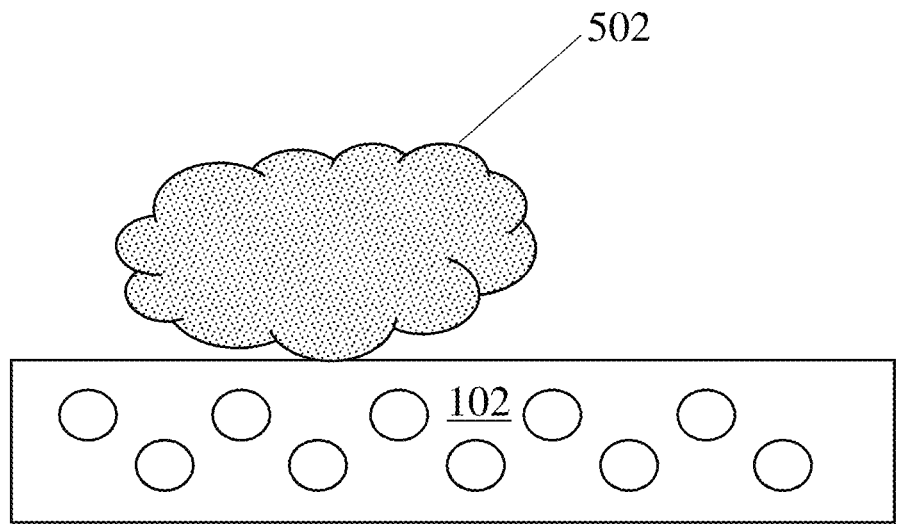
FIGS. 3A-3B show a method of sensing carbon dioxide, in accordance with some embodiments.

As also described elsewhere herein, in some embodiments, methods of sensing carbon dioxide are provided. One exemplary method of sensing carbon dioxide is shown in FIG. 3A. In FIG. 3A, a composition 102 is exposed to a gas or a liquid 502. The gas or liquid may comprise carbon dioxide and/or water. If the composition is exposed to a gas, the gas may have a relative humidity of greater than 0% RH (e.g., of greater than or equal to 1% RH and less than or equal to 100% RH). If the composition is exposed to a liquid, the liquid may have an equilibrium relative humidity of greater than 0% ERH (e.g., of greater than or equal to 1% ERH and less than or equal to 100% ERH). Exposure of a composition to a gas or liquid comprising carbon dioxide and water (e.g., a gas comprising carbon dioxide and having a relative humidity of greater than 0% RH, a liquid comprising carbon dioxide and having an equilibrium relative humidity of greater than 0% ERH) may be performed in a variety of suitable manners. For instance, in some embodiments, exposing a composition to a gas or liquid comprises placing the composition in an ambient environment comprising the gas or liquid. This may be accomplished, for instance, by placing the composition in the gas or liquid (e.g., by submerging the composition therein, by placing the composition in an ambient gaseous environment). As another example, in some embodiments, exposing a composition to a gas or liquid comprises introducing the gas or liquid into the ambient environment of the composition. This may be accomplished, for instance, by blowing a gas onto the composition, by pouring a liquid onto the composition, etc.).

Figure 3B:
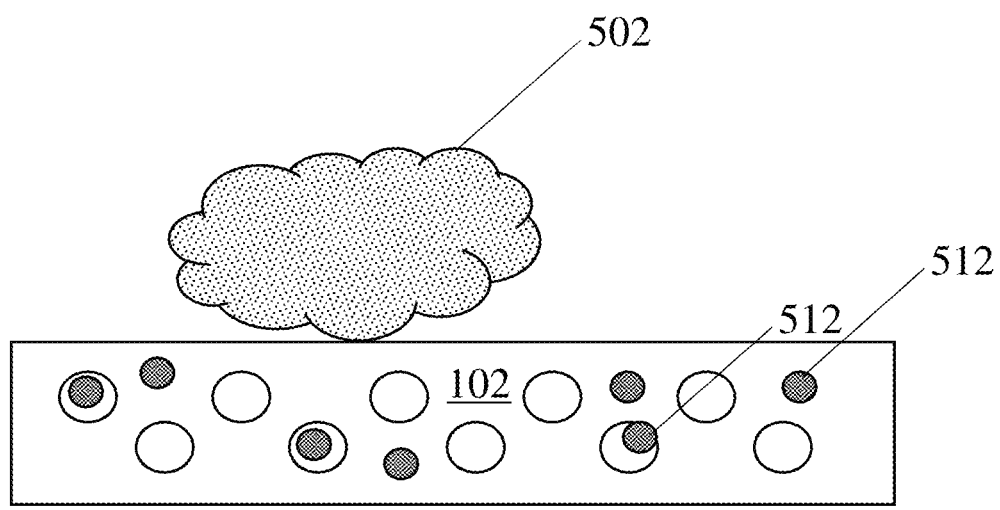

Upon exposure to the gas or liquid, a composition may undergo a structural, physical, and/or chemical change. By way of example, the composition may interact with a portion of one or more species present in the gas or liquid. For instance, as shown in FIG. 3B, a composition 102 may adsorb a species 512 present in the gas or liquid 502. A variety of suitable species present in gases and liquids may be interact with the composition (e.g., by adsorption thereonto). For instance, in some embodiments, water (e.g., in the form of humidity, in the form of one or more droplets) from a gas or liquid may be adsorbed onto the composition. As another example, additionally or alternatively, carbon dioxide from the gas or liquid may be adsorbed onto the composition. It is also possible that other, further, species present in the gas or liquid may be adsorbed onto the composition in some embodiments. A composition may adsorb all components of a gas to or liquid to which it is exposed, some components of a gas or liquid to which it is exposed, or no components of a gas or liquid to which it is exposed. The number and/or type of species in the gas or liquid adsorbed thereonto may vary with the number and/or type of species present in the gas or liquid.

A composition may adsorb a species present in a gas or liquid at a variety of suitable locations. For instance, as shown in FIG. 3B, in some embodiments, a species present in a gas or liquid may be adsorbed in a plurality of pores of a composition and/or may be adsorbed on a surface of a composition. It is also possible that other portions of a composition may adsorb a species present in a gas or liquid to which it is exposed. When a gas or liquid comprises more than one species, such as both water and carbon dioxide, the different species may be adsorbed onto different locations of the composition. In some embodiments, a species present in a gas or liquid adsorbs onto a composition through an interaction with another species adsorbed thereon. By way of example, in some embodiments, carbon dioxide present in a gas or liquid adsorbs on a composition by dissolving in water adsorbed thereon and/or by undergoing a reaction with water adsorbed thereon to form another species (e.g., a bicarbonate ion) that adsorbs onto the composition. Species adsorbing onto a composition, such as water and/or carbon dioxide, may do so by chemisorption and/or by physisorption.

As described elsewhere herein, in some embodiments, a composition as a whole has one or more features that are advantageous for sensing carbon dioxide. Such features may be evidenced by advantageous physical properties. For instance, a composition may adsorb water and/or carbon dioxide in relatively advantageous amounts and/or in relatively advantageous environments. As another example, a composition may exhibit an electrical resistivity that changes in an advantageous manner due to adsorption of water and/or carbon dioxide. Such properties will be described in further detail below.

As a first example, and as also described elsewhere herein, in some embodiments, the composition as a whole is configured to adsorb a relatively large amount of water from its ambient environment (e.g., even if that ambient environment is relatively low in humidity). This may be evidenced by the monolayer amount of water of the composition. As used herein, the monolayer amount of water of the composition refers to the wt % of water that can adsorb onto the surface of the composition to form a monolayer per mass of the composition. By way of example, if 10 g of water can adsorb onto a 100 g composition to form on a monolayer on the surface of the composition, the monolayer amount of water is 10 wt %. The monolayer amount of water of a composition may be determined in accordance with the procedure described in ISO 9277:2010(E) for the measurement of gas adsorption isotherms performed at 20° C. and for which water is the gas.

In some embodiments, a composition has a monolayer amount of water of greater than or equal to 2 wt %, greater than or equal to 2.5 wt %, greater than or equal to 3 wt %, greater than or equal to 4 wt %, greater than or equal to 5 wt %, greater than or equal to 7.5 wt %, greater than or equal to 10 wt %, greater than or equal to 12.5 wt %, greater than or equal to 15 wt %, or greater than or equal to 17.5 wt %. In some embodiments, a composition has a monolayer amount of water of less than or equal to 20 wt %, less than or equal to 17.5 wt %, less than or equal to 15 wt %, less than or equal to 12.5 wt %, less than or equal to 10 wt %, less than or equal to 7.5 wt %, less than or equal to 5 wt %, less than or equal to 4 wt %, less than or equal to 3 wt %, or less than or equal to 2.5 wt %. Combinations of the above-referenced ranges are also possible (e.g., from 2 wt % to 20 wt %, or from 5 wt % to 20 wt %). Other ranges are also possible.

Some compositions described herein readily uptake water to form a monolayer of water thereon. By way of example, some compositions may adsorb water to form a monolayer of water thereon upon exposure to a gas or liquid having a relatively low amount of water (e.g., upon exposure to a gas having a relatively low level of relative humidity, upon exposure to a liquid having a relatively low level of equilibrium relative humidity). Formation of the monolayer of water may be evidenced by a transition in a water adsorption isotherm from adsorption indicative of monolayer uptake to adsorption indicative of non-monolayer uptake as described in ISO 9277-2010 for the measurement of gas adsorption isotherms performed at 20° C. and for which water is the gas. In some embodiments, a composition uptakes water to form a monolayer of water thereon (and, optionally, uptakes further water beyond that forming a monolayer) upon exposure to a gas with a relative humidity of greater than or equal to 10% RH, greater than or equal to 12.5% RH, greater than or equal to 15% RH, greater than or equal to 17.5% RH, or greater than or equal to 20% RH. In some embodiments, a composition uptakes water to form a monolayer of water thereon (and, optionally, uptakes further water beyond that forming a monolayer) upon exposure to a liquid having an equilibrium relative humidity of greater than or equal to 10% ERH, greater than or equal to 12.5% ERH, greater than or equal to 15% ERH, greater than or equal to 17.5% ERH, or greater than or equal to 20% ERH.

Some compositions described herein may be configured to adsorb a relatively large amount of carbon dioxide from its ambient environment. This may be evidenced by the adsorption of carbon dioxide onto the composition in the relevant ambient environment. As used herein, the amount of carbon dioxide adsorbed onto the composition in a particular ambient environment refers to the wt % of carbon dioxide adsorbed onto the surface of the composition per mass of the composition in the particular ambient environment. By way of example, if 10 g of carbon dioxide adsorbs onto a 100 g composition in an ambient environment comprising less than or equal to 10,000 ppm of carbon dioxide, the amount of carbon dioxide adsorbed onto the composition is 10 wt % in an ambient environment comprising less than or equal to 10,000 ppm of carbon dioxide. The amount of carbon dioxide adsorbed onto the composition in a particular ambient environment may be determined in accordance with the procedure described in ISO 9277:2010(E) for the measurement of gas adsorption isotherms performed at 20° C. and for which carbon dioxide is the gas.

In some embodiments, an amount of carbon dioxide absorbed onto a composition described herein is particularly large. For instance, the amount of carbon dioxide absorbed onto the composition in an ambient environment comprising less than or equal to 10,000 ppm of carbon dioxide is greater than or equal to 0.1 wt %, greater than or equal to 0.15 wt %, greater than or equal to 0.2 wt %, greater than or equal to 0.25 wt %, greater than or equal to 0.3 wt %, greater than or equal to 0.35 wt %, greater than or equal to 0.4 wt %, greater than or equal to 0.45 wt %, or greater than or equal to 0.5 wt %. In some embodiments, the amount of carbon dioxide absorbed onto the composition in an ambient environment comprising less than or equal to 10,000 ppm of carbon dioxide is less than or equal to 1 wt %, less than or equal to 0.5 wt %, less than or equal to 0.45 wt %, less than or equal to 0.4 wt %, less than or equal to 0.35 wt %, less than or equal to 0.3 wt %, less than or equal to 0.25 wt %, less than or equal to 0.2 wt %, or less than or equal to 0.1 wt %. Combinations of the above-referenced ranges are also possible (e.g., from 0.1 wt % to 1 wt %, or from 0.5 wt % to 1 wt %). Other ranges are also possible.

In some embodiments, a composition is configured to exhibit a change in electrical resistivity upon exposure to a gas or liquid comprising carbon dioxide and water (e.g., to a gas having a relative humidity of greater than 0% RH, to a liquid having an equilibrium relative humidity of greater than or equal to 0% ERH). The gas or liquid causing the change in electrical resistivity may have one or more of the features described elsewhere herein. In other words, a composition may be configured to exhibit a change in electrical resistivity upon exposure to one or more of the gases described herein (e.g., a gas or liquid described herein comprising carbon dioxide, water, and, optionally, one or more further species). The change in electrical resistivity of a composition upon exposure to a gas or liquid comprising carbon dioxide, unless otherwise specified, may refer to the change in electrical resistivity as measured by a two-terminal technique or may refer to the change in electrical resistivity as measured by a four-terminal technique.

In some embodiments, a composition is configured to exhibit a change in electrical resistivity that is directly proportional to the amount of carbon dioxide in a gas or liquid at one or more amounts of water in the gas or liquid (e.g., at one or more values of relative humidity of a gas, at one or more values of equilibrium relative humidity of a liquid). For instance, a composition may be configured to exhibit a change in electrical resistivity that is directly proportional to the amount of carbon dioxide in the gas when the value of relative humidity of the gas is greater than or equal to 1% RH, greater than or equal to 2% RH, greater than or equal to 5% RH, greater than or equal to 7.5% RH, greater than or equal to 10% RH, greater than or equal to 15% RH, greater than or equal to 20% RH, greater than or equal to 25% RH, greater than or equal to 30% RH, greater than or equal to 40% RH, greater than or equal to 50% RH, greater than or equal to 60% RH, greater than or equal to 75% RH, greater than or equal to 80% RH, greater than or equal to 90% RH, greater than or equal to 95% RH, or greater than or equal to 99% RH. In some embodiments, a composition is configured to exhibit change in electrical resistivity that is directly proportional to the amount of carbon dioxide in the gas when the value of relative humidity of the gas is less than or equal to 100% RH, less than or equal to 99% RH, less than or equal to 95% RH, less than or equal to 90% RH, less than or equal to 80% RH, less than or equal to 75% RH, less than or equal to 60% RH, less than or equal to 50% RH, less than or equal to 40% RH, less than or equal to 30% RH, less than or equal to 25% RH, less than or equal to 20% RH, less than or equal to 15% RH, less than or equal to 10% RH, less than or equal to 7.5% RH, less than or equal to 5% RH, or less than or equal to 2% RH. Combinations of the above-referenced ranges are also possible (e.g., from 1% RH to 100% RH, from 10% RH to 90% RH, or from 20% RH to 80% RH). Other ranges are also possible.

A composition may be configured to exhibit a change in electrical resistivity that is directly proportional to an amount of carbon dioxide in a liquid when the value of equilibrium relative humidity of the liquid is greater than or equal to 1% ERH, greater than or equal to 2% ERH, greater than or equal to 5% ERH, greater than or equal to 7.5% ERH, greater than or equal to 10% ERH, greater than or equal to 15% ERH, greater than or equal to 20% ERH, greater than or equal to 25% ERH, greater than or equal to 30% ERH, greater than or equal to 40% ERH, greater than or equal to 50% ERH, greater than or equal to 60% ERH, greater than or equal to 75% ERH, greater than or equal to 80% ERH, greater than or equal to 90% ERH, greater than or equal to 95% ERH, or greater than or equal to 99% ERH. In some embodiments, a composition is configured to exhibit change in electrical resistivity that is directly proportional to the amount of carbon dioxide in the liquid when the value of equilibrium relative humidity of liquid is less than or equal to 100% ERH, less than or equal to 99% ERH, less than or equal to 95% ERH, less than or equal to 90% ERH, less than or equal to 80% ERH, less than or equal to 75% ERH, less than or equal to 60% ERH, less than or equal to 50% ERH, less than or equal to 40% ERH, less than or equal to 30% ERH, less than or equal to 25% ERH, less than or equal to 20% ERH, less than or equal to 15% ERH, less than or equal to 10% ERH, less than or equal to 7.5% ERH, less than or equal to 5% ERH, or less than or equal to 2% ERH. Combinations of the above-referenced ranges are also possible (e.g., from 1% ERH to 100% ERH, from 10% ERH to 90% ERH, or from 20% ERH to 80% ERH). Other ranges are also possible.

As would be known to one of ordinary skill in the art, the equilibrium relative humidity of a liquid refers to the relative humidity of air at the same temperature and pressure of the liquid with which the liquid would not exchange water under equilibrium conditions. By way of example, the water in a liquid having an equilibrium relative humidity of 50% ERH would be in thermodynamic equilibrium with the water in air at the same temperature and pressure having a relative humidity of 50% RH.

In some embodiments, a composition is configured to exhibit a change in electrical resistivity that is directly proportional to the amount of carbon dioxide in a gas or liquid when the amount of carbon dioxide in the gas or liquid is greater than or equal to 10 ppm, greater than or equal to 20 ppm, greater than or equal to 50 ppm, greater than or equal to 100 ppm, greater than or equal to 200 ppm, greater than or equal to 300 ppm, greater than or equal to 400 ppm, greater than or equal to 500 ppm, greater than or equal to 750 ppm, greater than or equal to 1000 ppm, greater than or equal to 1500 ppm, greater than or equal to 2000 ppm, greater than or equal to 2500 ppm, greater than or equal to 3000 ppm, greater than or equal to 5000 ppm, greater than or equal to 7500 ppm, greater than or equal to 10000 ppm, greater than or equal to 20000 ppm, greater than or equal to 50000 ppm, greater than or equal to 100000 ppm, greater than or equal to 200000 ppm, greater than or equal to 500000 ppm, greater than or equal to 750000 ppm, or greater than or equal to 900000 ppm. In some embodiments, a composition is configured to exhibit a change in electrical resistivity that is directly proportional to the amount of carbon dioxide in a gas or liquid when the amount of carbon dioxide in the gas or liquid is less than or equal to 990000 ppm, less than or equal to 900000 ppm, less than or equal to 750000 ppm, less than or equal to 500000 ppm, less than or equal to 200000 ppm, less than or equal to 100000 ppm, less than or equal to 50000 ppm, less than or equal to 20000 ppm, less than or equal to 10000 ppm, less than or equal to 7500 ppm, less than or equal to 5000 ppm, less than or equal to 3000 ppm, less than or equal to 2500 ppm, less than or equal to 2000 ppm, less than or equal to 1500 ppm, less than or equal to 1000 ppm, less than or equal to 750 ppm, less than or equal to 500 ppm, less than or equal to 400 ppm, less than or equal to 300 ppm, less than or equal to 200 ppm, less than or equal to 100 ppm, less than or equal to 50 ppm, or less than or equal to 20 ppm. Combinations of the above-referenced ranges are also possible (e.g., from 10 ppm 1 to 990000 ppm, from 400 ppm to 10000 ppm, or from 400 ppm to 2500 ppm). Other ranges are also possible.

In some embodiments, a composition is configured to exhibit a change in electrical resistivity that is directly proportional to the amount of carbon dioxide in a gas or liquid when the dependency of the electrical resistivity on the amount of carbon dioxide in the gas or liquid can be described by a linear equation and for which the actual electrical resistivity of the composition at any particular amount of carbon dioxide varies from that predicted by the linear equation by a relatively small amount. By way of example, in some embodiments, a best fit line can be drawn through the measured electrical resistivity of the composition upon exposure to gases or liquids comprising differing amounts of carbon dioxide, and, for each measured electrical resistivity, the absolute value of the ratio of the measured electrical resistivity to the difference between the measured electrical resistivity and the electrical resistivity of the composition predicted by the best fit line is greater than or equal to 3, greater than or equal to 3.5, greater than or equal to 4, greater than or equal to 4.5, greater than or equal to 5, greater than or equal to 6, greater than or equal to 7.5, greater than or equal to 10, greater than or equal to 12.5, greater than or equal to 15, greater than or equal to 17.5, or greater than or equal to 20. In some embodiments, a best fit line can be drawn through the measured electrical resistivity of the composition upon exposure to gases or liquids comprising differing amounts of carbon dioxide, and, for each measured electrical resistivity, the absolute value of the ratio of the measured electrical resistivity to the difference between the measured electrical resistivity and the electrical resistivity of the composition predicted by the best fit line is less than or equal to 50, less than or equal to 20, less than or equal to 17.5, less than or equal to 15, less than or equal to 12.5, less than or equal to 10, less than or equal to 7.5, less than or equal to 6, less than or equal to 5, less than or equal to 4.5, less than or equal to 4, or less than or equal to 3.5. Combinations of the above-referenced ranges are also possible (e.g., from 3 to 50). Other ranges are also possible.

As described above, a composition may be configured to exhibit a dependence of electrical resistivity on carbon dioxide that varies relatively little with the amount of water present in the gas or liquid comprising the carbon dioxide for some values of the water content of the gas or liquid (e.g., in the case of a gas, its relative humidity; in the case of a liquid, its equilibrium relative humidity). By way of example, in some embodiments, the magnitude of the change in electrical resistivity upon exposure to a liquid or gas comprising carbon dioxide varies less than or equal to 50%, less than or equal to 40%, less than or equal to 30%, less than or equal to 25%, less than or equal to 20%, less than or equal to 15%, less than or equal to 10%, less than or equal to 7.5%, less than or equal to 5%, less than or equal to 2%, or less than or equal to 1% within a specified range of relative humidities, equilibrium relative humidities and/or water contents. In some embodiments, the magnitude of the change in electrical resistivity upon exposure to a liquid or gas comprising carbon dioxide varies greater than or equal to 0%, greater than or equal to 1%, greater than or equal to 2%, greater than or equal to 5%, greater than or equal to 7.5%, greater than or equal to 10%, greater than or equal to 15%, greater than or equal to 20%, greater than or equal to 25%, greater than or equal to 30%, or greater than or equal to 40% within a specified range of relative humidities, equilibrium relative humidities, and/or water contents. Combinations of the above-referenced ranges are also possible (e.g., from 0% to 50%, or from 0% to 20%). Other ranges are also possible.

The values in the preceding paragraph may refer to the variation of electrical resistivity across gases or liquids having a variety of suitable ranges of water content. For instance, a composition may be configured to exhibit a dependence of electrical resistivity on carbon dioxide that has a variation with relative humidity in one or more of the ranges in the preceding paragraph upon exposure to a gas having a relative humidity of greater than or equal to 20% RH, greater than or equal to 25% RH, greater than or equal to 30% RH, greater than or equal to 35% RH, greater than or equal to 40% RH, greater than or equal to 45% RH, greater than or equal to 50% RH, or greater than or equal to 55% RH. A composition may be configured to exhibit a dependence of electrical resistivity on carbon dioxide that has a variation with relative humidity in one or more of the ranges in the preceding paragraph upon exposure to a gas having a relative humidity of less than or equal to 60% RH, less than or equal to 55% RH, less than or equal to 50% RH, less than or equal to 45% RH, less than or equal to 40% RH, less than or equal to 35% RH, or less than or equal to 30% RH. Combinations of the above-referenced ranges are also possible (e.g., from 20% RH to 60% RH). Other ranges are also possible.

A composition may be configured to exhibit a dependence of electrical resistivity on carbon dioxide that has a variation with equilibrium relative humidity in one or more of the ranges in the paragraph two paragraphs preceding upon exposure to a liquid having an equilibrium relative humidity of greater than or equal to 20% ERH, greater than or equal to 25% ERH, greater than or equal to 30% ERH, greater than or equal to 35% ERH, greater than or equal to 40% ERH, greater than or equal to 45% ERH, greater than or equal to 50% ERH, or greater than or equal to 55% ERH. A composition may be configured to exhibit a dependence of electrical resistivity on carbon dioxide that has a variation with equilibrium relative humidity in one or more of the ranges in the paragraph two paragraphs preceding upon exposure to a liquid having an equilibrium relative humidity of less than or equal to 60% ERH, less than or equal to 55% ERH, less than or equal to 50% ERH, less than or equal to 45% ERH, less than or equal to 40% ERH, less than or equal to 35% ERH, or less than or equal to 30% ERH. Combinations of the above-referenced ranges are also possible (e.g., from 20% ERH to 60% ERH). Other ranges are also possible.

As also described above, a composition may be configured to exhibit an enhanced response to carbon dioxide when exposed to a gas or liquid comprising both carbon dioxide and water in comparison to a gas or liquid comprising carbon dioxide but lacking water. In some embodiments, the change in electrical resistivity of the composition has a greater magnitude when exposed to a gas having a relative humidity of greater than or equal to 1% RH than when exposed to a gas having a relative humidity of less than 1% RH, the change in electrical resistivity of the composition has a greater magnitude when exposed to a gas having a relative humidity of greater than or equal to 5% RH than when exposed to a gas having a relative humidity of less than 0.5% RH, the change in electrical resistivity of the composition has a greater magnitude when exposed to a gas having a relative humidity of greater than or equal to 10% RH than when exposed to a gas having a relative humidity of less than 1% RH, or the change in electrical resistivity of the composition has a greater magnitude when exposed to a gas having a relative humidity of greater than or equal to 20% RH than when exposed to a gas having a relative humidity of less than 5% RH. Other ranges are also possible.

In some embodiments, the change in electrical resistivity of the composition has a greater magnitude when exposed to a liquid having an equilibrium relative humidity of greater than or equal to 1% ERH than when exposed to a liquid having an equilibrium relative humidity of less than 1% ERH, the change in electrical resistivity of the composition has a greater magnitude when exposed to a liquid having an equilibrium relative humidity of greater than or equal to 5% ERH than when exposed to a liquid having an equilibrium relative humidity of less than 0.5% ERH, the change in electrical resistivity of the composition has a greater magnitude when exposed to a liquid having an equilibrium relative humidity of greater than or equal to 10% ERH than when exposed to a liquid having an equilibrium relative humidity of less than 1% ERH, or the change in electrical resistivity of the composition has a greater magnitude when exposed to a liquid having an equilibrium relative humidity of greater than or equal to 20% ERH than when exposed to a liquid having an equilibrium relative humidity of less than 5% ERH. Other ranges are also possible.

In some embodiments, a composition described herein has one or more structural and/or chemical features that enhance its ability to sense carbon dioxide and/or to sense carbon dioxide in the presence of ambient water (e.g., ambient humidity). In other words, some compositions have particular structural and/or chemical features that cause them to have one or more of the beneficial performance features described elsewhere herein. Exemplary structural and chemical features that enhance composition performance for sensing carbon dioxide are described below. However, it should be understood that the structural and chemical features described below are not an exhaustive list of such structural and chemical features. Similarly, some embodiments may have one or more of structural and chemical features described below, and some embodiments may lack one or more of structural and chemical features described below.

One example of a structural feature that may enhance the utility of a composition for sensing carbon dioxide is a plurality of pores having a relatively small size. Small pores may confine carbon dioxide (and/or water) therein, promoting interaction between the carbon dioxide (and/or water) with the composition. Increased interaction between the carbon dioxide (and/or water) with the composition may enhance the response of the composition to the carbon dioxide (e.g., it may increase the magnitude of the change in the electrical resistivity of the composition caused by the exposure to the gas or liquid comprising the carbon dioxide). In some embodiments, the plurality of pores has an average diameter of greater than or equal to 0.25 nm, greater than or equal to 0.3 nm, greater than or equal to 0.4 nm, greater than or equal to 0.5 nm, greater than or equal to 0.6 nm, greater than or equal to 0.8 nm, greater than or equal to 1 nm, greater than or equal to 1.25 nm, greater than or equal to 1.5 nm, or greater than or equal to 1.75 nm. In some embodiments, the plurality of pores has an average diameter of less than or equal to 2 nm, less than or equal to 1.75 nm, less than or equal to 1.5 nm, less than or equal to 1.25 nm, less than or equal to 1 nm, less than or equal to 0.8 nm, less than or equal to 0.6 nm, less than or equal to 0.5 nm, less than or equal to 0.4 nm, or less than or equal to 0.3 nm. Combinations of the above-referenced ranges are also possible (e.g., from 0.25 nm to 2 nm, or from 0.3 nm to 1 nm). Other ranges are also possible. The average diameter of the plurality of pores may be determined by X-ray crystallography.

As used herein, pores refer to openings and/or voids in the composition. The pores may comprise open pores, closed pores, interconnected pores, and/or isolated pores.

Another example of a structural feature that may enhance the utility of the composition for sensing carbon dioxide is a two-dimensional structure. In some embodiments, a composition having a two-dimensional structure is strongly bonded together in two dimensions (e.g., by covalent bonding) and weakly bonded together in the third dimension (e.g., by van der Waals interactions). The two-dimensional structure may form a sheet that extends macro- or mesoscopically in two dimensions and has an Ångstrom-scale or nanometer-scale thickness in the third dimension. In some embodiments, the composition comprises a structural motif that repeats in two dimensions but is weakly ordered in the third dimension. Two-dimensional structures may be particularly useful for sensing carbon dioxide because they may exhibit enhanced sensitivity to carbon dioxide. For instance, adsorption of carbon dioxide to a two-dimensional structure may cause the a change in morphology along the weakly-bonded direction. This change in morphology may advantageously cause a change in electrical resistivity of the composition that has one or more of the advantageous features described elsewhere herein. However, it should also be understood that some compositions suitable for sensing carbon dioxide described herein may have morphologies other than two-dimensional structures. For instance, some compositions may have a three-dimensional structure.

In some embodiments, a composition described herein comprises one or more electrically conductive components. Without wishing to be bound by any particular theory, it is believed that the adsorption of carbon dioxide to many of the compositions described herein changes their electrical conductivities (i.e., it is believed to increase the electrical resistivity of n-type compositions and decrease the electrical resistivity of p-type compositions). Accordingly, compositions that are initially, as a whole, relatively electrically conductive and/or that comprise electrically conductive components may exhibit larger changes in electrical resistivity than compositions that are initially, as a whole, relatively electrically insulating. It is also believed that compositions that are initially, as a whole, relatively electrically conductive and/or that comprise electrically conductive components may have electrical resistivities and changes in electrical resistivity upon adsorption of carbon dioxide thereon that are in a range that is facile to detect.

In some embodiments, a composition comprises a molecule and/or an assembly of molecules comprising one or more electrically conductive pathways (e.g., a composition comprising a molecular structure comprising a backbone that is electrically conductive). The electrically conductive pathway(s) may comprise one or more functional groups configured to conduct electricity, such as a conjugated backbone, pi-pi stacking, and/or a redox active center. The composition may comprise one or more electrically conductive pathways having an electrical conductivity of greater than or equal to $10^{-9}$ S cm$^{-1}$, greater than or equal to $10^{-8}$ S cm$^{-1}$, greater than or equal to $10^{-7}$ S cm$^{-1}$, greater than or equal to $10^{-6}$ S cm$^{-1}$, greater than or equal to $10^{-5}$ S cm$^{-1}$, greater than or equal to $10^{-4}$ S cm$^{-1}$, greater than or equal to $10^{-3}$ S cm$^{-1}$, greater than or equal to $10^{-2}$ S cm$^{-1}$, greater than or equal to $10^{-1}$ S cm$^{-1}$, greater than or equal to 1 S cm$^{-1}$, greater than or equal to 10 S cm$^{-1}$, greater than or equal to 100 S cm$^{-1}$, or greater than or equal to 1000 S cm$^{-1}$. The composition may comprise one or more electrically conductive pathways having an electrical conductivity of less than or equal to 10000 S cm$^{-1}$, less than or equal to 1000 S cm$^{-1}$, less than or equal to 100 S cm$^{-1}$, less than or equal to 10 S cm$^{-1}$, less than or equal to 1 S cm$^{-1}$, less than or equal to $10^{-1}$ S cm$^{-1}$, less than or equal to $10^{-2}$ S cm$^{-1}$, less than or equal to $10^{-3}$ S cm$^{-1}$, less than or equal to $10^{-4}$ S cm$^{-1}$, less than or equal to $10^{-5}$ S cm$^{-1}$, less than or equal to $10^{-6}$ S cm$^{-1}$, less than or equal to $10^{-7}$ S cm$^{-1}$, or less than or equal to $10^{-8}$ S cm$^{-1}$. Combinations of the above-referenced ranges are also possible (e.g., from $10^{-9}$ S cm$^{-1}$ to 10000 S cm$^{-1}$, or from $10^{-6}$ S cm$^{-1}$ to 1 S cm$^{-1}$). Other ranges are also possible. The electrical conductivity of an electrically conductive pathway, unless otherwise specified, may refer to the electrical conductivity as measured by a two-terminal technique or may refer to the electrical conductivity as measured by a four-terminal technique.

Some compositions described herein may comprise a plurality of heteroatoms (i.e., a plurality of atoms other than carbon and hydrogen). The heteroatoms may be configured to interact with each other and/or with other components of the composition to provide a composition having a desirable structure (e.g., a structure comprising a plurality of pores having one or more of the advantageous features described elsewhere herein) and/or may be configured to interact with ambient water (e.g., ambient humidity) and/or carbon dioxide in a beneficial manner (e.g., the heteroatoms may promote adsorption of ambient water and/or carbon dioxide onto the composition and/or onto a plurality of pores therein). In some embodiments, at least a portion of the heteroatoms are chemically bonded (e.g., covalently) to a backbone that is electrically conductive (e.g., a backbone comprising carbon and hydrogen, a backbone as described elsewhere herein). Some compositions may comprise non-metal heteroatoms, such as nitrogen, oxygen, sulfur, selenium, and/or phosphorus. In some embodiments, a composition comprises both non-metal heteroatoms and metal ions. The non-metal heteroatoms may be bonded to the metal ions to form coordination complexes in such embodiments.

When a composition comprises a plurality of heteroatoms, the heteroatoms may be provided in the form of a variety of suitable functional groups. For instance, in some embodiments, a composition comprises a plurality of imine groups (comprising nitrogen heteroatoms), diimine groups (comprising nitrogen heteroatoms), and/or amine groups (comprising nitrogen atoms). In some embodiments, it may be desirable for the composition to comprise heteroatoms bonded to acidic protons. Without wishing to be bound by any particular theory, in some embodiments, it is believed that such acidic protons may be capable of forming hydrogen bonds with charged species formed upon adsorption of carbon dioxide to the composition (e.g., bicarbonate salts that may form in the presence of adsorbed water). In some embodiments, a composition comprises a plurality of heteroatoms that is Lewis basic.

As described above, some compositions described herein may comprise a plurality of metal ions (e.g., metal cations, such as transition metal cations). Like the heteroatoms described above, the metal ions may be configured to interact with each other and/or with other components of the composition to provide a composition having a desirable structure (e.g., a structure comprising a plurality of pores having one or more of the advantageous features described elsewhere herein) and/or may be configured to interact with ambient water (e.g., ambient humidity) and/or carbon dioxide in a beneficial manner (e.g., the metal ions may promote adsorption of ambient water and/or carbon dioxide onto the composition and/or onto a plurality of pores therein). As also described above, in some embodiments, metal ions are bonded to form coordination complexes with one or more other components of the composition (e.g., one or more heteroatoms therein, one or more ligands therein).

When a composition comprises a plurality of metal ions, the metal ions may comprise ions that are monovalent, divalent, and/or trivalent. Non-limiting examples of suitable metal ions include transition metal ions and/or noble metal ions ($Ag^+$, $Cu^+$, $Cu^{2+}$, $Fe^{2+}$, $Co^{2+}$, $Co^{3+}$, $Ni^+$, $Ni^{2+}$, $Pd^{2+}$, $Pt^{2+}$, $Ru^{2+}$, $Cd^{2+}$, $Zn^{2+}$, $Hg^{2+}$, $V^{2+}$, $V^{3+}$, $Cr^{2+}$, $Ti^{3+}$, $Sc^{3+}$, $Mn^{3+}$, $Cr^{3+}$) and post-transition metal ions (e.g., $Al^{3+}$, $In^{3+}$, $Ga^{3+}$).

In some embodiments, a composition comprises a metal-organic framework. In some embodiments, a metal-organic framework comprises a plurality of metal ions, each coordinated with at least one ligand comprising an imino-semiquinonate moiety. By way of example, the at least one ligand comprises at least two sets of ortho-diimine groups arranged about an organic core.

The term "metal-organic framework" is given its ordinary meaning in the art and refers to a one-, two-, or three-dimensional coordination polymer including metal ions and ligands which function as organic structural units, wherein a portion of the metal ions are each chemically bonded to at least one bi-, tri- or poly-dentate ligand. The metal ions, in addition to being coordinated with at least one organic structure unit, may also be bound to one or more auxiliary ligands, as described in more detail herein. When a composition as described herein comprises a metal-organic framework, the ligands therein may form a conductive backbone and/or comprise one of the heteroatoms described elsewhere herein. Similarly, when a composition as described herein comprises a metal-organic framework, the metal ions therein may comprise one or more of the metal ions described elsewhere herein. It should also be understood that a composition may comprise a metal-organic framework that comprises a plurality of pores as described elsewhere herein.

In some embodiments, a metal-organic framework comprises a plurality of metal ions, each coordinated with at least one ligand comprising at least two sets of ortho-diimine groups arranged about an organic core. In some embodiments, the at least one ligand comprises at least two ortho-phenylenediimine units. In some embodiments, a portion of the metal ions are associated with two, three, or four ligands, and each of those ligand is individually associated with one, two, three, or four metal ions. In some embodiments, a portion of the metal ions are associated with two ligands, and each of those ligands is individually associated with two metal ions. In some embodiments, a portion of the metal ions are associated with three ligands, and each of those ligands is individually associated with three metal ions. In some embodiments, a portion of the metal ions are associated with two ligands, and each of those ligands is individually associated with three metal ions. In some embodiments, a ligand is charged. In some embodiments, a ligand has a charge of (−1), or (−2), or (−3), or (−4). In some embodiments, a ligand has a charge of (−2).

In some embodiments, each ligand comprises two sets of ortho-diimine groups. In some embodiments, each ligand comprising two sets of ortho-diimine groups may be associated with two metal atoms. In some embodiments, each ligand comprises three sets of ortho-diimine groups. By way of example, in some embodiments, a metal-organic framework comprises hexaiminobenzene ligands and/or is formed from hexaiminobenzene ligands. In some embodiments, each ligand comprising three sets of ortho-diimine groups may be associated with three metal atoms. In some embodiments, each ligand comprises four sets of ortho-diimine groups. In some embodiments, each ligand comprising four sets of ortho-diimine groups may be associated with four metal atoms.

In some embodiments, the at least one ligand comprises at least two sets of ortho-phenylenediimine units. In some embodiments, the at least one ligand comprises two sets of ortho-phenylenediimine units. In some embodiments, the at least one ligand comprises three sets of ortho-phenylenediimine units. In some embodiments, the at least one ligand comprises four sets of ortho-phenylenediimine units.

The organic core comprising at least two set of ortho-diimine groups may be any suitable core. In some embodiments, the core is aromatic. Generally, the core comprises a rigid structure formed from fused aryl and/or heteroaryl rings. In some embodiments, the organic core comprises a plurality of fused aryl and/or heteroaryl rings. In some cases, the organic core comprises a plurality of fused aryl rings. In some cases, the organic core comprises one or more of benzyl, thiophenyl, carbazolyl, pyrrolyl, indolyl, and furanyl rings.

In some embodiments, the at least one ligand comprising at least two sets of ortho-diimine groups arranged about an organic core comprises the structure:

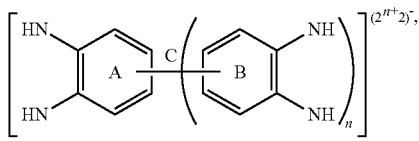

wherein n is 1, 2, or 3, and C represent one or more bonds formed between ring A and each ring B. In some cases, n is 1. In some cases, n is 2. In some cases, n is 3.

In some embodiments, the at least one ligand comprises the structure:

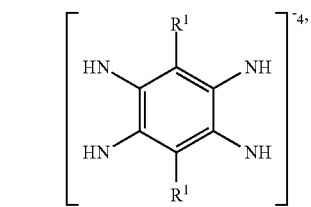

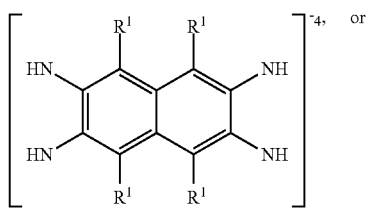

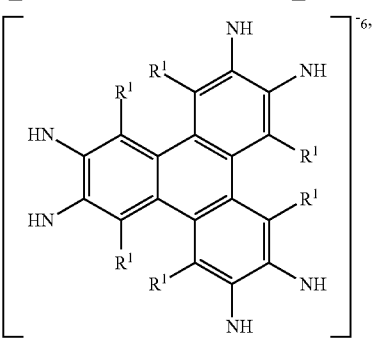

wherein each $R^1$ is the same or different and is selected from the group consisting of hydrogen, —$NO_2$, —R', —F, —Cl, —Br, —I, —CN, —NC, —$SO_3$R', —$SO_3$H, —OR', —OH, —SR', —SH, —$PO_3$R', —$PO_3$H, —$CF_3$, —NR'$_2$, —NHR', and —$NH_2$, wherein each R' is the same or different and is optionally substituted alkyl or optionally substituted aryl. In some embodiments, the at least one ligand comprises the structure:

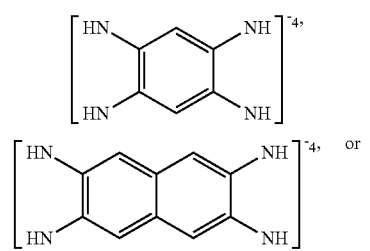

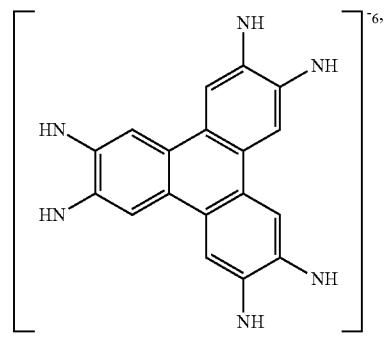

Other non-limiting examples of ligands include:

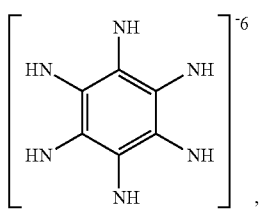

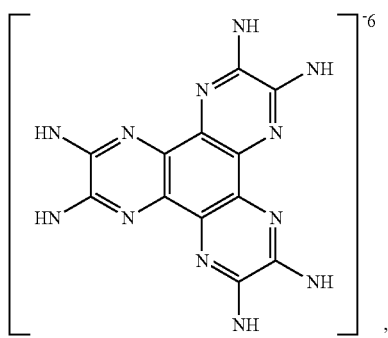

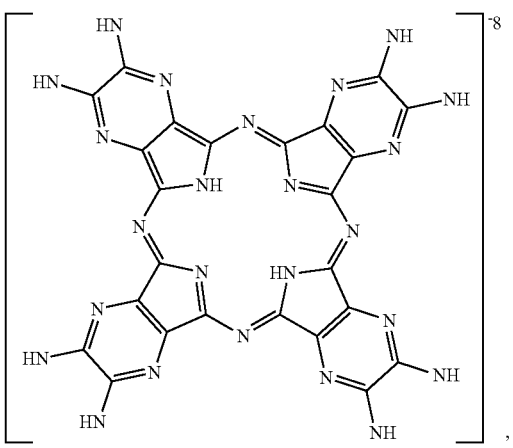

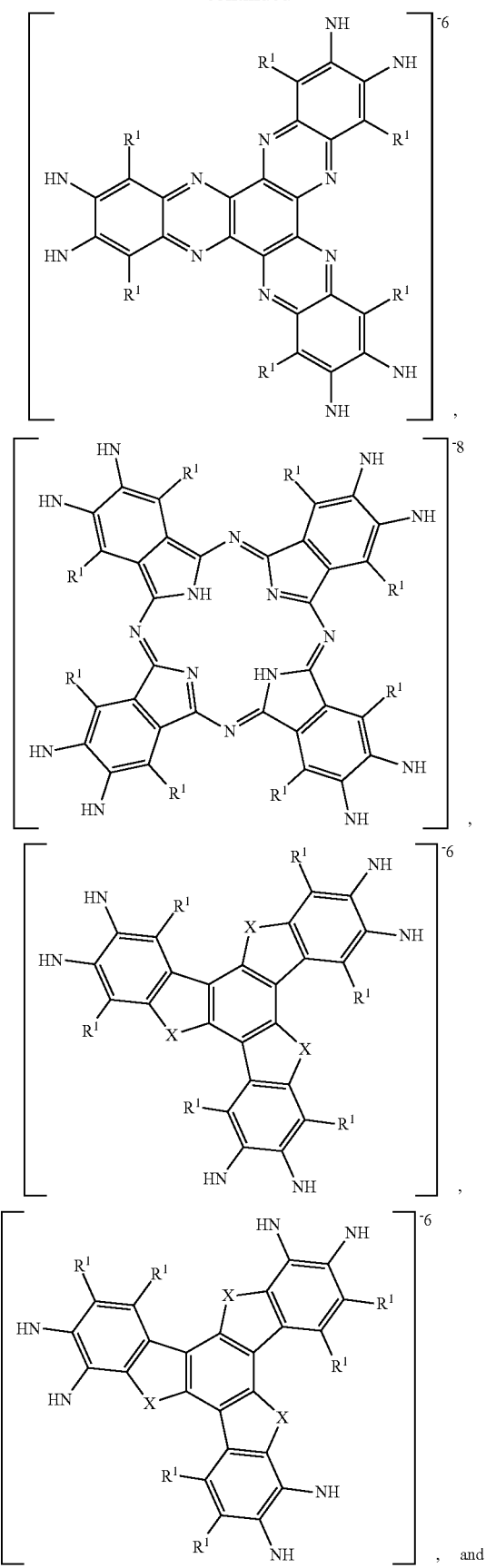

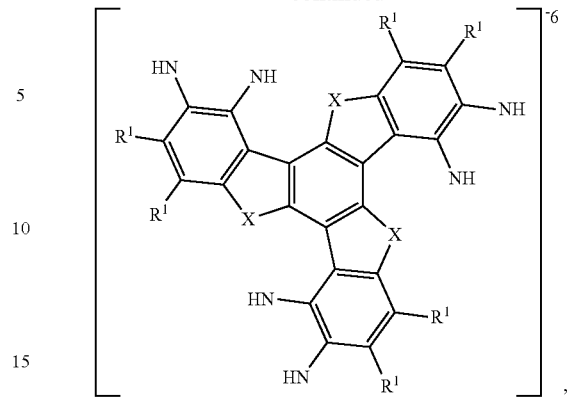

wherein each R¹ is the same or different and is selected from the group consisting of hydrogen, —$NO_2$, —R', —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$; each X is the same or different and is selected from the group consisting of NR', O, S, Se, and Te; and each R' is the same or different and is optionally substituted alkyl or optionally substituted aryl. In some embodiments, each R¹ is hydrogen. In some embodiments, each X is the same or different and is selected from the group consisting of NR', O, and S. In some embodiments, each X is NR'. In some embodiments, each X is O. In some embodiments, each X is S. In some embodiments, each X is Se. In some embodiments, each X is Te. In some embodiments, each R' is H.

In some embodiments, more than one type of ligand may be employed, for example, a first type of ligand and a second type of ligand. The two or more types of ligands may be provided in any suitable ratio. The two or more types of ligands may be provided in any suitable ratio.

Any suitable metal ion may be employed, including those described elsewhere herein. Each metal ion may be a monovalent, divalent, or trivalent. In some embodiments, each metal ion is a monovalent metal ion. Non-limiting examples of monovalent metal ions are $Ag^+$, $Cu^+$, and $Au^+$. In some cases, the metal ion is $Cu^+$. In some embodiments, the metal ion is a divalent metal ion. Non-limiting examples of monovalent metal ions are $Mg^{2+}$, $Mn^{2+}$, $Fe^{2+}$, $Co^{2+}$, $Ni^{2+}$, $Cu^{2+}$, $Pd^{2+}$, $Pt^{2+}$, $Ru^{2+}$, $Cd^{2+}$, $Zn^{2+}$, $Pb^{2+}$, $Hg^{2+}$, $V^{2+}$, $Cr^{2+}$, and $Ni^{2+}$. In some cases, the metal ion is $Ni^{2+}$. In some cases, the metal ion is $Cu^{2+}$. In some embodiments, the metal ion is a trivalent metal ion. Non-limiting examples of trivalent metal ions are $Fe^{3+}$, $V^{3+}$, $Ti^{3+}$, $Sc^{3+}$, $Al^{3+}$, $In^3$, $Ga^{3+}$, $Mn^{3+}$, $Co^{3+}$, and $Cr^{3+}$. In some embodiments, a metal-organic framework may comprise two or more metal ions having a different valency. For example, the metal organic framework may comprise one or more monovalent metal ion and one or more divalent metal ion. In some such embodiments, the one or more ligand may be redox active and/or able to accommodate the different redox states of the metal ion. In some embodiments, the one or more metal ions may be the same metal ion but in different redox states (e.g., $Cu^+$ and $Cu^{2+}$).

In some embodiments, a composition comprises a metal-organic framework comprising copper ions and hexaiminobenzene ligands. By way of example, a composition may comprise copper-hexaiminobenzene.

In some embodiments, more than one type of metal ion may be employed, for example, a first type of metal ion and a second type of metal ion. In some cases, the first type of metal ion and the second type of metal ion have the same valency. For example, the first type of metal ion may be a first type divalent metal ion and the second type of metal ion may be a second type of divalent metal ion. The two or more types of metal ions may be provided in any suitable ratio.

In some embodiments, a metal ion may be associated with one or more auxiliary ligands. In some cases, the one or more auxiliary ligands may be found above and/or below the metal ion (e.g., as apical ligands). An auxiliary ligand may or might not be charged. Non-limiting examples of auxiliary ligands include halides (e.g., chlorine, fluorine, bromine, iodine), other salts (e.g., nitrate, carbonate, sulfonate, etc.), and coordinating solvents (e.g., water, pyridine, tetrahydrofuran, diethyl ether, etc.).

When present, the metal-organic frameworks described herein may be synthesized by a variety of suitable methods. In some cases, a method of synthesizing a metal-organic framework comprises exposing a plurality of metal ions to a plurality of precursor ligands in the presence of an oxidant and a base to form a metal-organic framework comprising a portion of the plurality of metal ions each coordinated with at least one ligand, wherein each ligand comprises at least two sets of ortho-diimine groups arranged about an organic core. Non-limiting examples of ligands comprises at least two sets of ortho-diimine groups arranged about an organic core are described herein. In some embodiments, the metal ion is provided as a salt, and the at least one precursor ligand provided comprises at least two sets of ortho-diamine groups. During the course of the reaction, the diamine groups of the precursor ligand are oxidized into the corresponding diimine group, which coordinates with a metal ion. In some cases, the precursor ligand comprises at least two sets of ortho-phenylenediamine groups, and during the course of the reaction, the precursor ligand is oxidized so that each ortho-phenylenediamine group is transformed into an ortho-phenylenediimine group, which coordinates with a metal ion.

The metal ion and the precursor ligand may be provided in any suitable amounts. In some embodiments, the mole ratio of the metal ion to the precursor ligand may be based upon the coordination of the metal ion to the ligand. For example, in embodiments where the ligand is coordinated with three metal ions, and each metal ion is associated with two ligands, the mole ratio of the metal ion to the precursor ligand may be about least 3:2. As another example, in embodiments, where the ligand is coordinated with two metal ions, and each metal ion is associated with one ligand, the mole ratio of the metal ion to the precursor ligand may about 2:1. In some embodiments, the precursor ligand is providing in slight mole excess as compared to the metal ion.

In some embodiments, the metal ions are provided as a salt. Non-limiting examples of salts chloride, fluoride, bromide, iodide, triflate, $BF_4$, $PF_6$, $NO_3^-$, $SO_4^{2-}$, and $ClO_4^-$ salts. In some cases, the salt is $SO_4^{2-}$.

In some embodiments, the at least one precursor ligand comprising at least two sets of ortho-diamine groups arranged about an organic core comprises the structure:

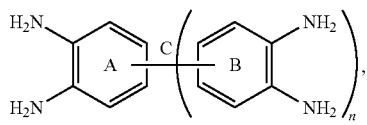

wherein n is 1, 2, or 3, and C represent one or more bonds formed between ring A and each ring B. In some cases, n is 1. In some cases, n is 2. In some cases, n is 3.

In some embodiments, the at least one precursor ligand comprises the structure:

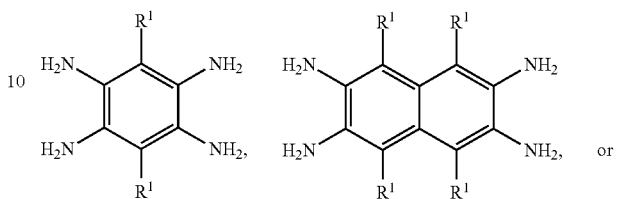

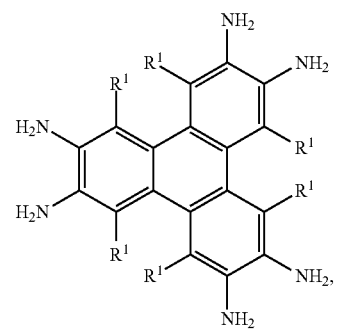

wherein each $R^1$ is the same or different and is selected from the group consisting of hydrogen, $-NO_2$, $-R'$, $-F$, $-Cl$, $-Br$, $-I$, $-CN$, $-NC$, $-SO_3R'$, $-SO_3H$, $-OR'$, $-OH$, $-SR'$, $-SH$, $-PO_3R'$, $-PO_3H$, $-CF_3$, $-NR'_2$, $-NHR'$, and $-NH_2$, wherein each R' is the same or different and is optionally substituted alkyl or optionally substituted aryl. In some embodiments, the at least one precursor ligand comprises the structure:

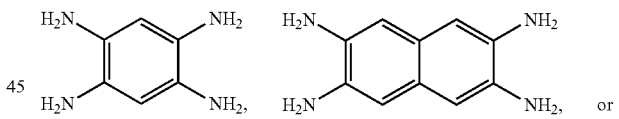

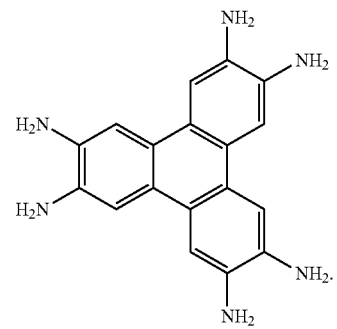

Other non-limiting examples of precursor ligands include:

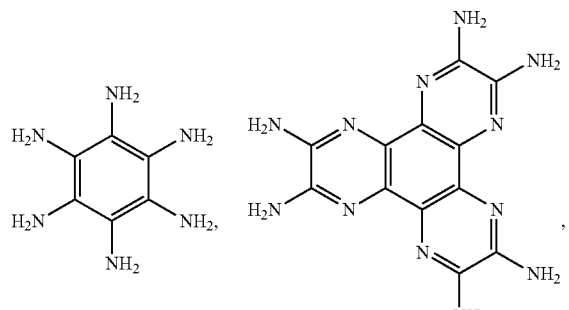

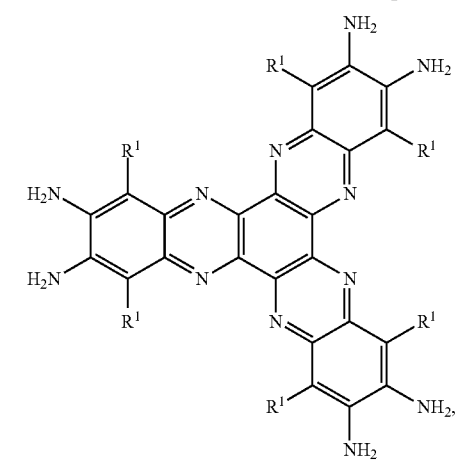

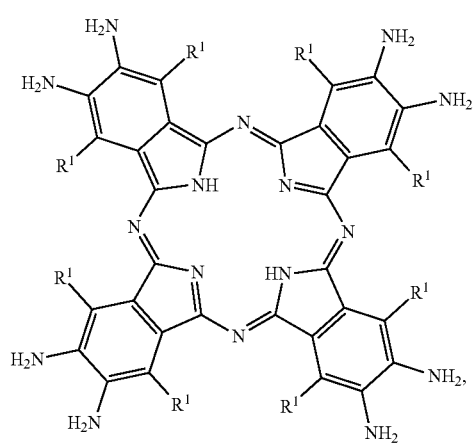

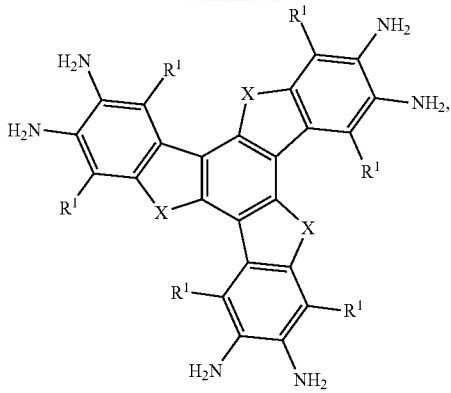

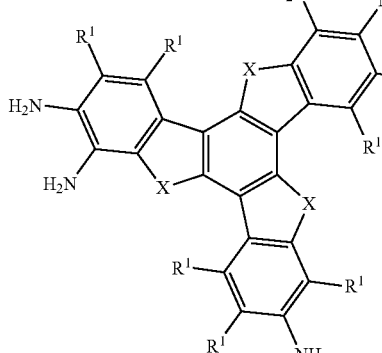

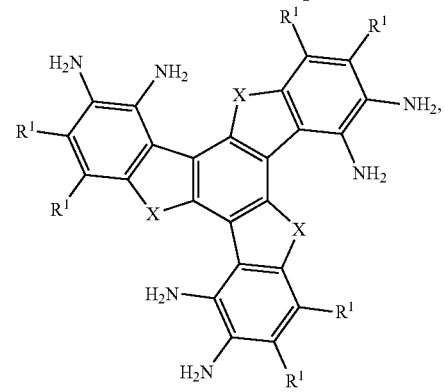

wherein each $R^1$ is the same or different and is selected from the group consisting of hydrogen, —$NO_2$, —R', —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$; each X is the same or different and is selected from the group consisting of NR', O, S, Se, and Te; and each R' is the same or different and is optionally substituted alkyl or optionally substituted aryl. In some embodiments, each $R^1$ is hydrogen. In some embodiments, each X is the same or different and is selected from the group consisting of NR', O, and S. In some embodiments, each X is NR'. In some embodiments, each X is O. In some embodiments, each X is S. In some embodiments, each X is Se. In some embodiments, each X is Te. In some embodiments, each R' is H.

Any suitable base may be utilized in the synthetic methods described herein. Non-limiting examples of bases include $NR''_3$ wherein each R" is the same or different and is hydrogen, optionally substituted alkyl, or optionally substituted aryl; QOH, wherein Q is a cation (e.g., a metal cation, a semi-metal cation, $NH_4$); acetate. In some embodiments, the base is $NH_3$ or $NH_4OH$. In some embodiments, the base is selected to have a higher pH as compared to the amino groups on the precursor ligand.

Any suitable oxidant may be employed. In some embodiments, the oxidant is oxygen. In some embodiments, the oxidant is a chemical oxidant. Non-limiting examples of oxidants include air, oxygen, ferricinium, nitrosonium, $Ag^{2+}$, $Ag^+$, $Fe^{3+}$, $MnO_4^-$, and $CrO_4^-$. The oxidant may be present in an amount suitable to aid in the oxidation of the precursor ligand. In some embodiments, the oxidant is present in excess.

Any suitable solvent may be utilized in the synthetic methods described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. In some embodiments, the solvent is water.

The methods of synthesis described herein may be carried out at any suitable temperature. In some cases, the reaction is carried out at about room temperature (e.g., 25° C., 20° C., from 20° C. to 25° C., or the like). In some cases, however, the reaction is carried out at temperatures below or above room temperature. In some embodiments, the reaction is carried at a temperature from 25° C. to 100° C., from 35° C. to 95° C., from 45° C. to 85° C., or from 55° C. to 75° C.

Metal-organic frameworks synthesized using the methods described herein may be purified using techniques known to those of ordinary skill in the art. In some embodiments, a synthesized metal-organic framework may be washed, sometimes involving a Soxhlet extractor, boiled, and/or sonicated (e.g., to remove excess starting materials).

The synthetic methods described herein may provide for rapid synthesis of a wide range of metal-organic frameworks. The ability to synthesize metal-organic frameworks rapidly may be useful for the screening of known, as well as new metal-organic frameworks, to determine its appropriateness for sensing carbon dioxide in a gas having an ambient humidity of greater than 0% RH or a liquid having an equilibrium relative humidity of greater than 0% ERH.

The metal-organic frameworks described herein, in some cases, may be formed as a film on a surface of a material. The film may be formed using techniques known to those of ordinary skill in the art. For example, the film may be formed by spin-casting method, drop-casting method, dip coating method, roll coating method, screen coating method, a spray coating method, screen printing method, ink-jet method, and the like. In some cases, the thickness of the film may be less than or equal to 100 microns, less than or equal to 10 microns, less than or equal to 1 micron, less than or equal to 100 nm, less than or equal to 10 nm, or less than or equal to 1 nm. In some cases, the film may have a thickness greater than or equal to 1 mm. Other ranges are also possible. The thickness of the film may be measured by microscopy.

In some embodiments, the metal-organic frameworks comprise little or no excess metal ions. That is, the metal-organic frameworks may comprise essentially no metal ions which are not coordinated with a ligand comprising at least two ortho-diimine groups (i.e., "free metal ions"). In some embodiments, the metal-organic framework comprises less than or equal to 0.5 wt %, less than or equal to 0.4 wt %, less than or equal to 0.3 wt %, less than or equal to 0.2 wt %, less than or equal to 0.1 wt %, less than or equal to 0.05 wt %, less than or equal to 0.03 wt %, less than or equal to 0.02 wt %, less than or equal to 0.01 wt %, less than or equal to 0.005 wt %, or less than or equal to 0.001 wt % of free metal ions. Those of ordinary skill in the art will be aware of methods for determining the amount of free metal ions, for example, using XPS.

The compositions described herein may be exposed to a variety of suitable gases and liquids. The gas or liquid may comprise a variety of suitable species, such as carbon dioxide, water, nitrogen, oxygen, argon, helium, and/or carbon monoxide. In some embodiments, a composition described herein is exposed to air, such as air comprising carbon dioxide and water.

As described above, a gas or liquid to which a composition is exposed may comprise water. The water may be in gaseous form (e.g., dissolved in another gas, such as air) and/or may be in liquid form (e.g., in the form of liquid droplets suspended in a gas, such as air, or dissolved in another liquid). When the water is present as a gas dissolved in another gas, the gas may have a variety of suitable relative humidities. For instance, in some embodiments, a gas to which a composition is exposed has a relative humidity of greater than or equal to 1% RH, greater than or equal to 2% RH, greater than or equal to 5% RH, greater than or equal to 7.5% RH, greater than or equal to 10% RH, greater than or equal to 15% RH, greater than or equal to 20% RH, greater than or equal to 25% RH, greater than or equal to 30% RH, greater than or equal to 40% RH, greater than or equal to 50% RH, greater than or equal to 60% RH, greater than or equal to 75% RH, greater than or equal to 90% RH, greater than or equal to 95% RH, or greater than or equal to 99% RH. In some embodiments, a gas to which a composition is exposed has a relative humidity of less than or equal to 100% RH, less than or equal to 99% RH, less than or equal to 95% RH, less than or equal to 90% RH, less than or equal to 75% RH, less than or equal to 60% RH, less than or equal to 50% RH, less than or equal to 40% RH, less than or equal to 30% RH, less than or equal to 25% RH, less than or equal to 20% RH, less than or equal to 15% RH, less than or equal to 10% RH, less than or equal to 7.5% RH, less than or equal to 5% RH, or less than or equal to 2% RH. Combinations of the above-referenced ranges are also possible (e.g., from 1% RH to 100% RH, or from 10% RH to 90% RH). Other ranges are also possible. It should also be understood that some embodiments may relate to gases comprising both gaseous water and liquid water. Such gases would be understood to have a relative humidity in excess of 100%.

When the water is present as a gas dissolved in a liquid, the liquid may have a variety of suitable equilibrium relative humidities. For instance, in some embodiments, a liquid to which a composition is exposed has an equilibrium relative humidity of greater than or equal to 1% ERH, greater than or equal to 2% ERH, greater than or equal to 5% ERH, greater than or equal to 7.5% ERH, greater than or equal to 10% ERH, greater than or equal to 15% ERH, greater than or equal to 20% ERH, greater than or equal to 25% ERH, greater than or equal to 30% ERH, greater than or equal to 40% ERH, greater than or equal to 50% ERH, greater than or equal to 60% ERH, greater than or equal to 75% ERH, greater than or equal to 90% ERH, greater than or equal to 95% ERH, or greater than or equal to 99% ERH. In some embodiments, a liquid to which a composition is exposed has an equilibrium relative humidity of less than or equal to 100% ERH, less than or equal to 99% ERH, less than or equal to 95% ERH, less than or equal to 90% ERH, less than or equal to 75% ERH, less than or equal to 60% ERH, less than or equal to 50% ERH, less than or equal to 40% ERH, less than or equal to 30% ERH, less than or equal to 25% ERH, less than or equal to 20% ERH, less than or equal to 15% ERH, less than or equal to 10% ERH, less than or equal to 7.5% ERH, less than or equal to 5% ERH, or less than or equal to 2% ERH. Combinations of the above-referenced ranges are also possible (e.g., from 1% ERH to 100% ERH, or from 10% ERH to 90% ERH). Other ranges are also possible. In some embodiments, a liquid to which a composition is exposed comprises an amount of water that has an equilibrium relative humidity of greater than 100% ERH.

A gas or liquid to which a composition is exposed may comprise a variety of suitable amounts of carbon dioxide. In some embodiments, the gas or liquid comprises carbon dioxide in an amount of greater than or equal to 50 ppm, greater than or equal to 75 ppm, greater than or equal to 100 ppm, greater than or equal to 125 ppm, greater than or equal to 150 ppm, greater than or equal to 200 ppm, greater than or equal to 250 ppm, greater than or equal to 300 ppm, greater than or equal to 350 ppm, greater than or equal to 400 ppm, greater than or equal to 450 ppm, greater than or equal to 500 ppm, greater than or equal to 600 ppm, greater than or equal to 800 ppm, greater than or equal to 1000 ppm, greater than or equal to 2000 ppm, greater than or equal to 5000 ppm, greater than or equal to 7500 ppm, greater than or equal to 10000 ppm, greater than or equal to 20000 ppm, greater than or equal to 50000 ppm, or greater than or equal to 75000 ppm. In some embodiments, the gas or liquid comprises carbon dioxide in an amount of less than or equal to 100000 ppm, less than or equal to 75000 ppm, less than or equal to 50000 ppm, less than or equal to 20000 ppm, less than or equal to 10000 ppm, less than or equal to 7500 ppm, less than or equal to 5000 ppm, less than or equal to 2000 ppm, less than or equal to 1000 ppm, less than or equal to 800 ppm, less than or equal to 600 ppm, less than or equal to 500 ppm, less than or equal to 450 ppm, less than or equal to 400 ppm, less than or equal to 350 ppm, less than or equal to 300 ppm, less than or equal to 250 ppm, less than or equal to 200 ppm, less than or equal to 150 ppm, less than or equal to 125 ppm, less than or equal to 100 ppm, or less than or equal to 75 ppm. Combinations of the above-referenced ranges are also possible (e.g., from 50 ppm to 100000 ppm, or from 400 ppm to 10000 ppm). Other ranges are also possible.

For convenience, certain terms employed in the specification, examples, and appended claims are listed here. Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R'") wherein R', R", and R'" each independently represent a group permitted by the rules of valence.

The terms "acyl," "carboxyl group," or "carbonyl group" are recognized in the art and can include such moieties as can be represented by the general formula:

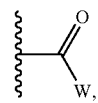

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

EXAMPLE 1

This Example relates to the fabrication and testing of a composition exhibiting advantageous properties for sensing carbon dioxide in a gas having a relative humidity of greater than 0% RH. In this Example, the composition is a copper-hexaiminobenzene two-dimensional metal-organic framework.

More specifically, this Example describes a new ambient carbon dioxide chemiresistor platform based on nanoporous and conductive two-dimensional metal-organic frameworks. It is found that two-dimensional metal-organic frameworks that comprise N-heteroatoms incorporated in the form of imino-semiquinonate moieties exhibit desirable chemiresistive responsiveness to carbon dioxide. Here, it is shown that copper-hexaiminobenzene reliably and quickly senses carbon dioxide when present at 400-2500 ppm in air. The ambient carbon dioxide sensitivity was found to be nearly independent of the relative humidity, with the overall highest sensitivity to carbon dioxide for air having an ambient humidity of 10-80% RH. Without wishing to be bound by any particular theory, it is believed that the copper-hexaiminobenzene two-dimensional metal-organic framework exhibits this sensitivity to carbon dioxide due its nanoporosity. It is also believed that the nanoporosity of the copper-hexaiminobenzene two-dimensional metal-organic framework causes the copper-hexaiminobenzene two-dimensional metal-organic framework to have a relatively high density of carbon dioxide adsorption sites and that these carbon dioxide adsorption sites remain autogenously hydrated in ambient environments having relative humidities typical of ambient environments in which carbon dioxide sensors are employed even if the relative humidity of the ambient environment fluctuates.

Figure 4A:
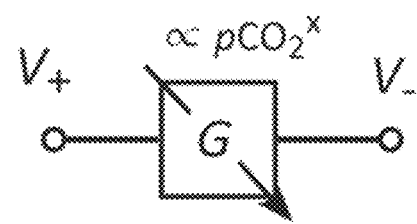
FIG. 4A shows a schematic depiction of a shift in conductance upon exposure to carbon dioxide, in accordance with some embodiments.

In one design, a two-dimensional metal-organic framework, such as a copper-hexaiminobenzene two-dimensional metal-organic framework, could be employed as a passive chemiresistive component of a simple two-terminal device. Chemical interactions between ambient carbon dioxide and the two-dimensional metal-organic framework could cause a shift in one or more current-voltage (I-V) characteristic of the device, such as a shift in the direct-current conductance (FIG. 4A).

Figure 4B:
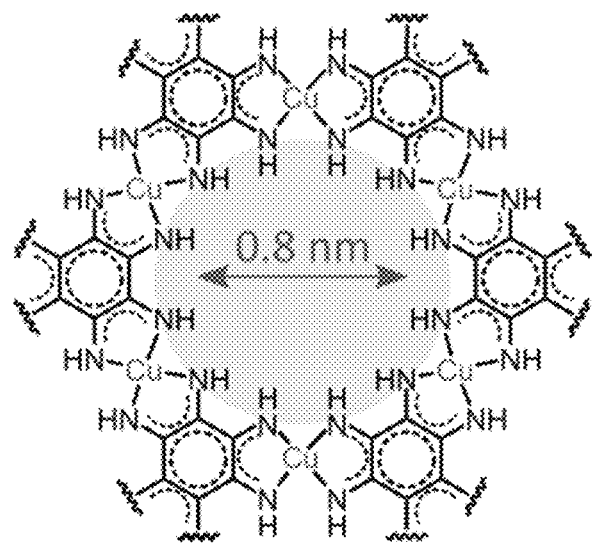
FIG. 4B shows a schematic depiction of a copper-hexaiminobenzene metal-organic framework, in accordance with some embodiments.

As described above, one suitable two-dimensional metal-organic framework for carbon dioxide sensing is copper-hexaiminobenzene (FIG. 4B). Other compositions, such as other metal-organic frameworks, that comprise some or all of the following features may also be suitable: (1) a conjugated backbone, (2) Lewis-basic N-heteroatoms, (3) protons (which may promote hydrogen-bond stabilization of charged species), (4) a plurality of pores having a relatively small diameter (e.g., nanopores having a diameter of approximately 0.8 nm, which it is believed strike a balance between the ease with which the carbon dioxide can reach the interaction sites and the confinement of the carbon dioxide, and which it is believed results in improved interaction between the carbon dioxide and the composition), (5) a plurality of hydrophilic pores, which may be the same plurality of pores and the plurality of pores having the relatively small diameter, and which it is believed promote hydration of the sites at which the MOF and the carbon dioxide interact over a broad range of the ambient relative humidity. It is also believed that some of the above-mentioned features may additionally enhance the ability of compositions to sense other, non-carbon dioxide gases, such as other gases that are soluble in water and/or other gases for which the presence of moisture typically affects the ease with which they may be sensed.

Figure 4C:
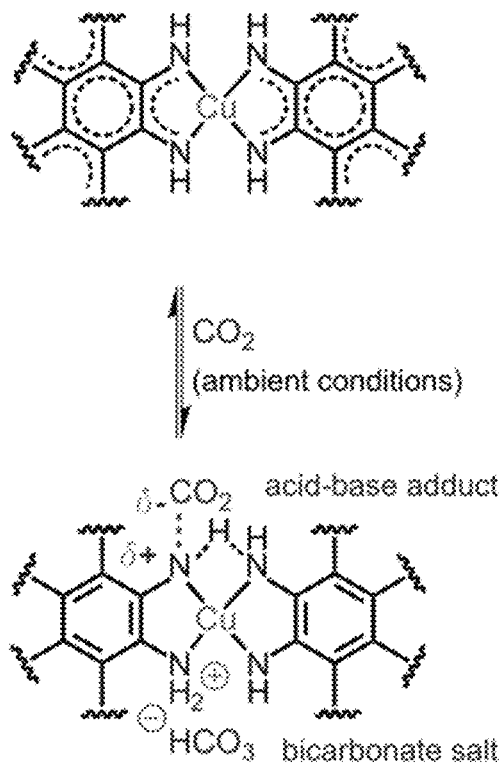
FIG. 4C shows a schematic depiction of an interaction between carbon dioxide and a copper-hexaiminiobenzene metal-organic framework, in accordance with some embodiments.

Similar to other amine-rich solids, it is conceivable that the compositions described herein, such as compositions having one or more of the features described in the preceding paragraph, could reversibly form carbon dioxide adducts and/or bicarbonate salts. It is believed that these species may give rise to charge trapping, which it is believed may cause electronic modulation of the conjugated backbone of the relevant structure (FIG. 4C).

Figure 4D:
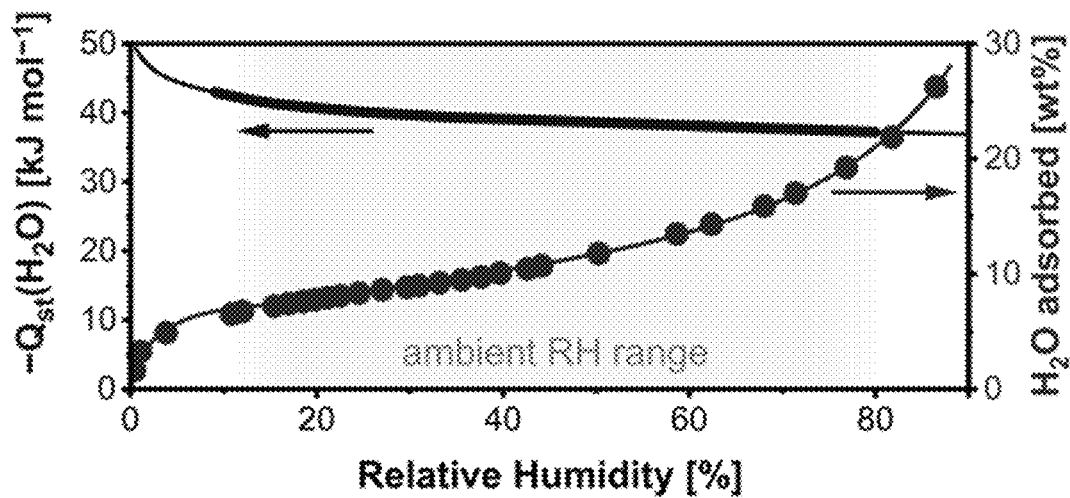
FIG. 4D shows a water adsorption isotherm of a copper-hexaiminobenzene metal-organic framework, in accordance with some embodiments.
Figure 4E:
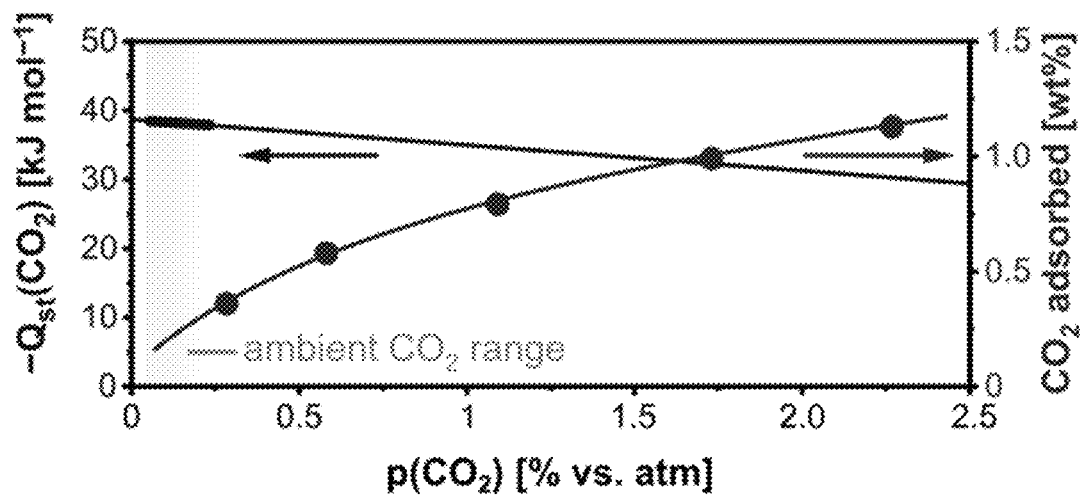
FIG. 4E shows the fitted head of adsorption of carbon dioxide on a copper-hexaiminobenzene metal-organic framework, in accordance with some embodiments.

The water adsorption isotherm of a copper-hexaiminobenzene two-dimensional metal-organic framework shows distinct monolayer uptake between 0% RH and 5-10% RH (FIG. 4D). The fitted Langmuir and BET monolayer amounts in the 0-20% RH range are ~8.1 wt % and ~6.2 wt %, respectively, which are consistent with filling of the sub-nanometer diameter pores under these conditions. By contrast, the much more gradual uptake at higher RH is indicative of structure-extrinsic multilayer adsorption on grain boundaries and other structural defects. For this reason, it is believed that the hydration of the intrinsic pores stays roughly unchanged at values of relative humidity greater than 10% RH. The fitted heat of adsorption of water on the copper-hexaiminobenzene two-dimensional metal-organic framework is relatively small (approx. 35-45 kJ mol$^{-1}$), indicating weak physisorption. Additionally, the fitted heat of adsorption of carbon dioxide on the copper-hexaiminobenzene two-dimensional metal-organic framework is in this same range (approx. 35-40 kJ mol$^{-1}$; FIG. 4E). Thus, it is believed that exchange of adsorbed water with carbon dioxide may occur without a significant energy penalty. Although the measured heat of adsorption for water on the copper-hexaiminobenzene two-dimensional metal-organic framework is small, it is believed that water will spontaneously condense on the surface of the copper-hexaiminobenzene two-dimensional metal-organic framework. This is believed to be beneficial for promoting the adsorption of carbon dioxide on the copper-hexaiminobenzene two-dimensional metal-organic framework because the heat of adsorption for non-condensable carbon dioxide on the copper-hexaiminobenzene two-dimensional metal-organic framework is believed to be large but (as described above) the heat of adsorption for carbon dioxide on the copper-hexaiminobenzene two-dimensional metal-organic framework is similar to that of water. This phenomenon is believed to be consistent with the favorable formation of acid-base adducts between carbon dioxide and the N-heteroatoms in the pores of the copper-hexaiminobenzene two-dimensional metal-organic framework in the presence of water.

Figure 5A:
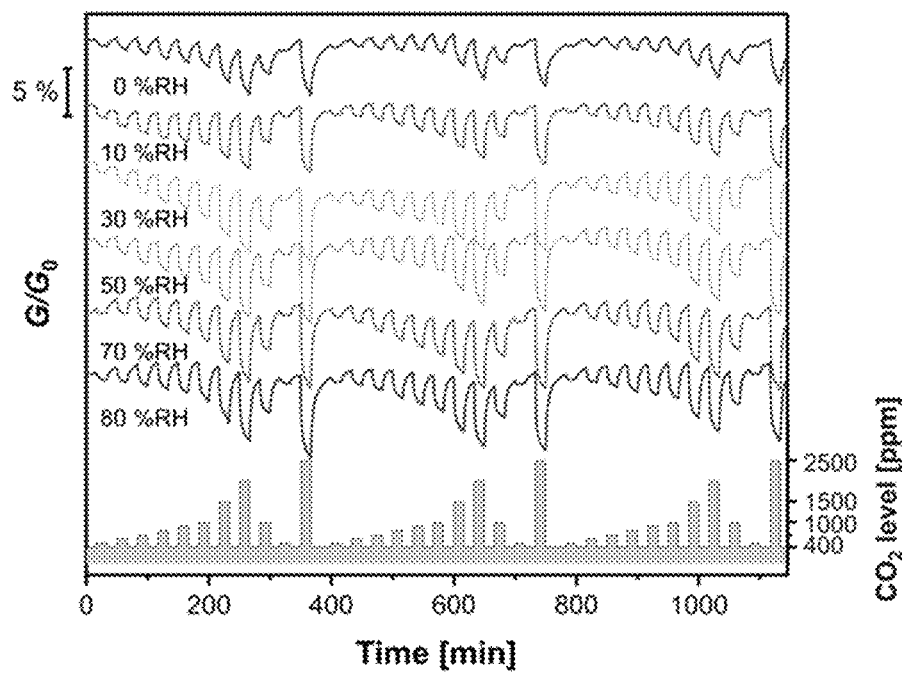
FIG. 5A shows normalized conductometric and conductance traces for a carbon dioxide sensor, in accordance with some embodiments.
Figure 5B:
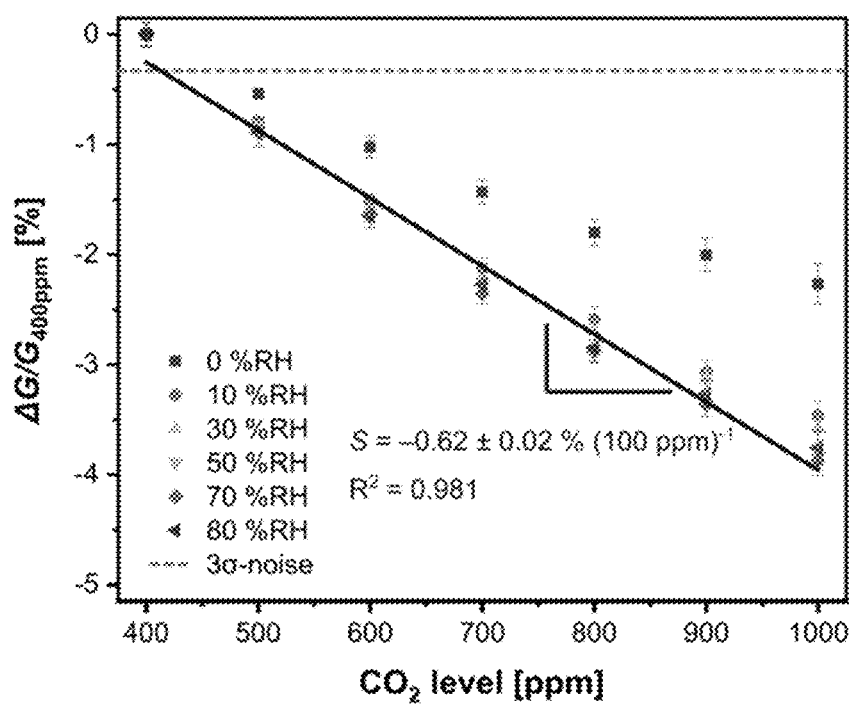
FIG. 5B shows the normalized response of sensors to carbon dioxide at varying carbon dioxide levels for air comprising 500-1000 ppm carbon dioxide, in accordance with some embodiments.

Chemiresistive sensors were fabricated by drop casting as-synthesized copper-hexaiminobenzene two-dimensional metal-organic frameworks onto interdigitated printed electrodes on ceramic substrates. The chemiresistive sensors were then loaded in parallel into an in-house gas sensing cell, in which they were initially conditioned for several hours under constant electrical bias and simulated ambient conditions to perform a baseline stabilization. After baseline stabilization, the direct-current conductometric (I-t) measurements were performed on the chemiresistive sensors at room temperature and during a sequenced exposure to 400-2500 ppm levels of carbon dioxide. It is noted that outdoor atmospheres typically comprise approximately 400 ppm of carbon dioxide and that indoor atmospheres typically comprise less than or equal to 2500 ppm. These experiments were repeated on an unchanged set of 10 devices at different constant relative humidities ranging from 0% RH to 80% RH. The normalized conductometric (I-t) and conductance (G/Go, where Go is the initial baseline current) traces were recorded for a representative device (FIG. 5A). A "turn-off" response, in which the conductance of the device was inverse proportional to the concentration of carbon dioxide in the air, was clearly observed in these experiments. Moreover, the observed effect was highly repeatable over one week of continuous experimentation. The normalized response of the sensors to carbon dioxide at varying carbon dioxide levels ($\Delta G/G_{400ppm}$) for air comprising 500-1000 ppm carbon dioxide are plotted as a function of carbon dioxide FIG. 5B. Over the broad range of ambient conditions (10-80% RH) tested, these results show an approximately linear and relative humidity-independent relationship between the carbon dioxide level and the sensor response.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of sensing carbon dioxide substantially independently of humidity, comprising:
    exposing a composition to a gas and/or a liquid, wherein:
        the composition comprises a molecular structure comprising an electrically conductive backbone, a plurality of heteroatoms, and a plurality of pores,
        the composition has a monolayer amount of water greater than or equal to 2 wt % versus a total weight of the composition,
        the gas and/or the liquid comprises carbon dioxide in an amount greater than or equal to 400 ppm and less than or equal to 10,000 ppm, and
        the gas has a relative humidity greater than or equal to 10% RH and/or the liquid has an equilibrium relative humidity greater than or equal to 10% ERH, wherein:
        the composition is configured to exhibit an electrical resistivity dependence on the amount of carbon dioxide in the gas, wherein the electrical resistivity dependence on the amount of carbon dioxide in the gas changes by less than 50% when the relative humidity of the gas is from 10% RH to 80% RH, and/or
        the composition is configured to exhibit an electrical resistivity dependence on the amount of carbon dioxide in the liquid, wherein the electrical resistivity dependence on the amount of carbon dioxide in the liquid changes by less than 50% when the equilibrium relative humidity of the liquid is from 10% ERH to 80% ERH.

2. A sensor configured to sense carbon dioxide substantially independently of humidity, comprising:
    a composition,
    wherein:
        the composition comprises a molecular structure comprising an electrically conductive backbone, a plurality of heteroatoms, and a plurality of pores,
        the composition has a monolayer amount of water greater than or equal to 2 wt % versus a total weight of the composition, and
        the composition is configured to exhibit a change in electrical resistivity upon exposure to a gas comprising carbon dioxide and having a relative humidity greater than or equal to 10% RH and/or the composition is configured to exhibit the change in electrical resistivity upon exposure to a liquid comprising carbon dioxide and having an equilibrium relative humidity greater than or equal to 10% ERH,
    wherein:
        the composition is configured to exhibit an electrical resistivity dependence on an amount of carbon dioxide in the gas, wherein the electrical resistivity dependence on the amount of carbon dioxide in the gas changes by less than 50% when the relative humidity of the gas is from 10% RH to 80% RH, and/or
        the composition is configured to exhibit an electrical resistivity dependence on an amount of carbon dioxide in the liquid, wherein the electrical resistivity dependence on the amount of carbon dioxide in the liquid changes by less than 50% when the equilibrium relative humidity of the liquid is from 10% ERH to 80% ERH.

3. A sensor configured to sense carbon dioxide substantially independently of humidity, comprising:
    a metal-organic framework,
    wherein:
        the metal-organic framework is configured to exhibit a change in electrical resistivity upon exposure to a gas comprising carbon dioxide and having a relative humidity greater than 10% RH and/or the metal-organic framework is configured to exhibit the change in electrical resistivity upon exposure to a liquid comprising carbon dioxide and having an equilibrium relative humidity greater than or equal to 10% ERH, and
        the change in electrical resistivity is directly proportional to an amount of carbon dioxide in the gas when the relative humidity of the gas is from 10% RH to 80% RH and/or the change in electrical resistivity is directly proportional to an amount of carbon dioxide in the liquid when the equilibrium relative humidity of the liquid is from 10% ERH to 80% ERH, wherein:

the metal-organic framework is configured to exhibit an electrical resistivity dependence on the amount of carbon dioxide in the gas, wherein the electrical resistivity dependence on the amount of carbon dioxide in the gas changes by less than 50% when the relative humidity of the gas is from 10% RH to 80% RH, and/or the metal-organic framework is configured to exhibit an electrical resistivity dependence on the amount of carbon dioxide in the liquid, wherein the electrical resistivity dependence on the amount of carbon dioxide in the liquid changes by less than 50% when the equilibrium relative humidity of the liquid is from 10% ERH to 80% ERH.

4. A sensor as in claim 2, wherein the composition comprises a metal-organic framework.

5. A sensor as in claim 2, wherein the plurality of heteroatoms comprises a nitrogen atom, and wherein the nitrogen atom forms a component of an amino group.

6. A sensor as in claim 2, wherein the plurality of heteroatoms comprises a nitrogen atom, and wherein the nitrogen atom forms a component of an imino group.

7. A sensor as in claim 2, wherein the molecular structure comprises at least one ligand comprising at least two sets of ortho-diimine groups arranged about an organic core, and wherein the at least one ligand comprising at least two sets of ortho-diimine groups arranged about an organic core is a hexaiminobenzene moiety.

8. A sensor as in claim 2, wherein the amount of carbon dioxide in the gas and/or the liquid is greater than or equal to 400 ppm and less than or equal to 10,000 ppm.

9. A sensor as in claim 2, wherein the relative humidity of the gas is from 10% RH to 80% RH.

10. A sensor as in claim 2, wherein the equilibrium relative humidity of the liquid is from 10% ERH to 80% ERH.

11. A sensor as in claim 2, wherein the composition is configured to exhibit the change in electrical resistivity upon exposure to the gas comprising the carbon dioxide.

12. A sensor as in claim 2, wherein the change in electrical resistivity is directly proportional to the amount of carbon dioxide in the gas when the relative humidity of the gas is from 10% RH to 80% RH and/or the change in electrical resistivity is directly proportional to the amount of carbon dioxide in the liquid when the equilibrium relative humidity of the liquid from 10% ERH to 80% ERH.

13. A sensor as in claim 2, wherein the composition is configured to uptake water such that, upon exposure to a gas with a relative humidity of greater than or equal to 10% RH, the monolayer amount of water is greater than or equal to 5 wt. % versus a total weight of the composition.

14. A sensor as in claim 2, wherein adsorption of carbon dioxide onto the composition in an ambient environment comprising less than or equal to 10000 ppm of carbon dioxide is greater than or equal to 0.5 wt % versus a total weight of the composition.

15. A sensor as in claim 2, wherein the composition is disposed on a plurality of electrodes.

16. A sensor as in claim 2, wherein the sensor is configured to determine the change in the electrical resistivity upon exposure to the gas or the liquid.

17. A sensor as in claim 2, wherein the monolayer amount of water is greater than or equal to 5 wt % versus a total weight of the composition.

18. A sensor as in claim 2, wherein the composition comprises a plurality of pores.

19. A sensor as in claim 2, wherein the change in electrical resistivity is directly proportional to the amount of carbon dioxide in the gas when the relative humidity of the gas is from 10% RH to 80% RH.

20. A method as in claim 1, wherein:
the electrical resistivity dependence on the amount of carbon dioxide in the gas changes by less than 25% when the relative humidity of the gas is from 10% RH to 80% RH, and/or
the electrical resistivity dependence on the amount of carbon dioxide in the liquid changes by less than 25% when the equilibrium relative humidity of the liquid is from 10% ERH to 80% ERH.

21. A method as in claim 1, wherein:
the electrical resistivity dependence on the amount of carbon dioxide in the gas changes by less than 15% when the relative humidity of the gas is from 10% RH to 80% RH, and/or
the electrical resistivity dependence on the amount of carbon dioxide in the liquid changes by less than 15% when the equilibrium relative humidity of the liquid is from 10% ERH to 80% ERH.

22. A sensor as in claim 2, wherein:
the electrical resistivity dependence on the amount of carbon dioxide in the gas changes by less than 25% when the relative humidity of the gas is from 10% RH to 80% RH, and/or
the electrical resistivity dependence on the amount of carbon dioxide in the liquid changes by less than 25% when the equilibrium relative humidity of the liquid is from 10% ERH to 80% ERH.

23. A sensor as in claim 2, wherein:
the electrical resistivity dependence on the amount of carbon dioxide in the gas changes by less than 15% when the relative humidity of the gas is from 10% RH to 80% RH, and/or
the electrical resistivity dependence on the amount of carbon dioxide in the liquid changes by less than 15% when the equilibrium relative humidity of the liquid is from 10% ERH to 80% ERH.

24. A sensor as in claim 3, wherein:
the electrical resistivity dependence on the amount of carbon dioxide in the gas changes by less than 25% when the relative humidity of the gas is from 10% RH to 80% RH, and/or
the electrical resistivity dependence on the amount of carbon dioxide in the liquid changes by less than 25% when the equilibrium relative humidity of the liquid is from 10% ERH to 80% ERH.

25. A sensor as in claim 3, wherein:
the electrical resistivity dependence on the amount of carbon dioxide in the gas changes by less than 15% when the relative humidity of the gas is from 10% RH to 80% RH, and/or
the electrical resistivity dependence on the amount of carbon dioxide in the liquid changes by less than 15% when the equilibrium relative humidity of the liquid is from 10% ERH to 80% ERH.

* * * * *